United States Patent
Moriya

(10) Patent No.: US 8,260,557 B2
(45) Date of Patent: Sep. 4, 2012

(54) SYSTEM AND METHOD FOR DETECTING PARTICLE GENERATION SOURCE, AND STORAGE MEDIUM THEREFOR

(75) Inventor: Tsuyoshi Moriya, Nirasaki (JP)

(73) Assignee: Tokyo Electron Limited, Tokyo (JP)

( * ) Notice: Subject to any disclaimer, the term of this patent is extended or adjusted under 35 U.S.C. 154(b) by 315 days.

(21) Appl. No.: 12/398,523

(22) Filed: Mar. 5, 2009

(65) Prior Publication Data

US 2009/0228215 A1    Sep. 10, 2009

Related U.S. Application Data

(60) Provisional application No. 61/055,568, filed on May 23, 2008.

(30) Foreign Application Priority Data

Mar. 6, 2008 (JP) ................................ 2008-056431

(51) Int. Cl.
 *G01N 31/00* (2006.01)
 *G06F 17/18* (2006.01)
 *G06F 19/00* (2006.01)

(52) U.S. Cl. ............. 702/22; 702/179; 702/35; 702/29; 702/81; 702/108; 702/127; 702/181; 702/182; 702/183; 324/762.01

(58) Field of Classification Search ..................... 702/22, 702/179, 181
See application file for complete search history.

(56) References Cited

U.S. PATENT DOCUMENTS

| | | | | |
|---|---|---|---|---|
| 6,466,895 B1* | 10/2002 | Harvey et al. | ................. | 702/181 |
| 2005/0027476 A1* | 2/2005 | Lim | ............................. | 702/179 |
| 2006/0212245 A1* | 9/2006 | Chityala et al. | ................. | 702/81 |
| 2006/0246683 A1* | 11/2006 | Pan et al. | ...................... | 438/424 |
| 2007/0076942 A1* | 4/2007 | Yatsugake et al. | ............ | 382/141 |
| 2007/0099310 A1* | 5/2007 | Vepa et al. | ........................ | 438/4 |

FOREIGN PATENT DOCUMENTS

JP  8-189896  7/1996
KR  10-2003-0067457  8/2003

OTHER PUBLICATIONS

Office Action issued Jan. 10, 2011, in Korea Patent Application No. 10-2009-0018646.

* cited by examiner

*Primary Examiner* — Cindy H Khuu
*Assistant Examiner* — Timothy H Hwang
(74) *Attorney, Agent, or Firm* — Oblon, Spivak, McClelland, Maier & Neustadt, L.L.P.

(57) ABSTRACT

A system for determining occurrence factors of particles includes a user interface device, and an apparatus for detecting the occurrence factors of particles. The apparatus for detecting the occurrence factors of particles includes a storage unit that stores a program for executing a calculation method for calculating a likelihood of each of the occurrence factors of particles in the form of a score; and a calculation unit for calculating the score for each of the occurrence factors of particles based on particle distributions at least on a surface of a substrate using the stored program. The user interface device displays the calculated score for each of the occurrence factors of particles.

8 Claims, 23 Drawing Sheets

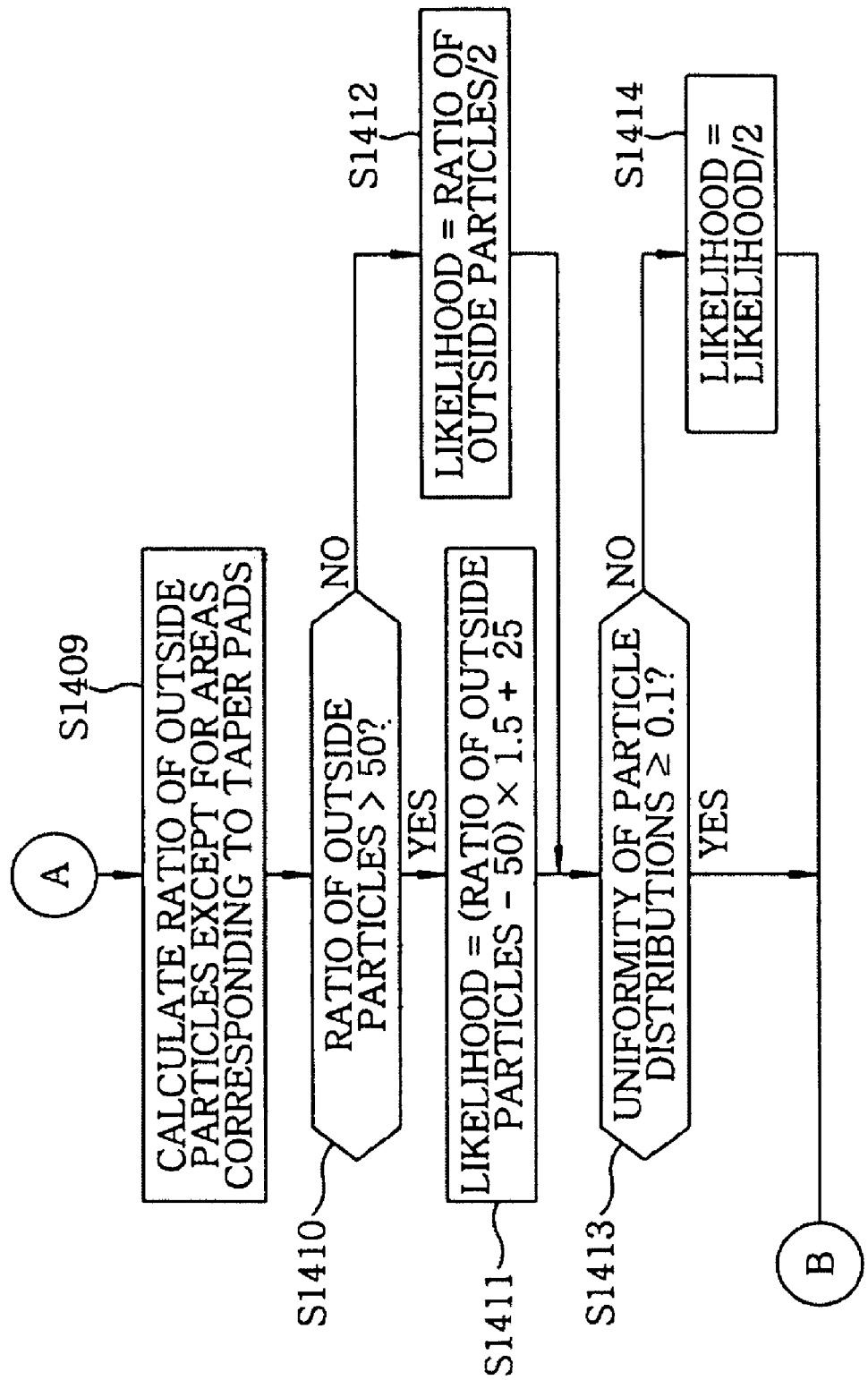

DISTANCE FROM CENTER OF MAP (mm)

SYSTEM AND METHOD FOR DETECTING PARTICLE GENERATION SOURCE, AND STORAGE MEDIUM THEREFOR

FIELD OF THE INVENTION

The present invention relates to a system and method for detecting particle generation source, and a storage medium for recording the method; and, more particularly, to a system for detecting the occurrence factors of particles, which determines the occurrence factors of particles generated in a substrate processing system which performs specific processing on a substrate.

BACKGROUND OF THE INVENTION

Generally, a substrate processing system includes process modules for performing plasma processing on a semiconductor wafer (hereinafter simply referred to as a "wafer" (that is, a substrate) using plasma, and a transfer module or a loader module for conveying wafers between the corresponding process modules and Front Opening Unified Pods (FOUPs) (that is, containers for accommodating wafers). In the substrate processing system, particles may adhere to wafers when the plasma processing is performed on the wafers or when the wafers are conveyed. The adhered particles cause defects in semiconductor devices fabricated using the wafers. Accordingly, there is a need to prevent the particles from adhering to the wafers.

Particles are generated due to various factors, such as a mechanical contact between a wafer and a component part and a chemical reaction between a processing gas and some other material. In the substrate processing system, a large number of semiconductor devices are fabricated by performing plasma processing on a lot of wafers. If the occurrence factors of particles are not removed, the yield of the semiconductor devices becomes extremely low. Accordingly, in the substrate processing system, it is very important to determine the occurrence factors of particles and to remove the corresponding occurrence factors.

Accordingly, there have been proposed various conventional methods of fully testing particles adhered to a wafer and detecting the occurrence factors of particles based on the test results. In more detail, there was proposed a method of easily detecting the occurrence factors of particles by acquiring the distributions of the particles in a wafer in the form of an alien substance map and by automatically classifying the particles in the corresponding alien substance map (for example, refer to Japanese Patent Application Publication No. H8-189896).

However, in order to determine the occurrence factors of particles based on the classification results of the particles, there is a need for a knowledgeable technician who is familiar with the occurrence factors of particles (for example, a technician who works for a manufacturer that manufactures a substrate processing system), even though the corresponding classification results appear on the alien substance map in the above-described method.

Furthermore, the substrate processing system is installed not in the factory of the manufacturer that manufactures the corresponding substrate processing system but in the factory of a customer who purchases the corresponding substrate processing system. Thus, the manufacturer's technician cannot always be near the substrate processing system. Consequently, when particles adhere to a wafer, a person who first determines the occurrence factors of particles is the customer's technician.

The corresponding customer's technician generally does not have detailed knowledge of the occurrence factors of particles. Accordingly, although the results of the classification of the particles are obtained, there is a problem in that the occurrence factors of particles cannot be accurately determined. For this reason, strange results, such as a reduction in the rate of operation of the substrate processing system, come about because the corresponding substrate processing system is stopped until the manufacturer's technician arrives at the customer's factory.

SUMMARY OF THE INVENTION

In view of the above, the present invention provides a system and method for detecting the occurrence factors of particles and a storage medium for recording the method which enables even a person who has little skill regarding the occurrence factors of particles to accurately determine them.

In accordance with one aspect of the present invention, there is provided a system for determining occurrence factors of particles, comprising a user interface device; and an apparatus for detecting the occurrence factors of particles. The apparatus for detecting the occurrence factors of particles includes a storage unit that stores a program for executing a calculation method for calculating a likelihood of each of the occurrence factors of particles in the form of a score; and a calculation unit for calculating the score for each of the occurrence factors of particles based on particle distributions at least on a surface of a substrate using the stored program. Further, the user interface device displays the calculated score for each of the occurrence factors of particles.

Preferably, the calculation unit calculates the score based on at least one of a material, shape and size of the particles.

Preferably, the calculation unit determines whether to calculate the score depending on a type of a substrate processing system using the stored program.

Preferably, the storage unit is capable of storing a program for executing a calculation method for calculating a likelihood of a new occurrence factor of particles in the form of a score.

Preferably, the occurrence factors of particles respectively corresponding to the programs for executing the calculation methods stored in the storage unit include at least one of local contact in peripheral portions of the substrate, rubbing between the substrate and a member surrounding the corresponding substrate, particles generated in the member to surround the substrate, gas hole penetration, crystal originated particles, deposited residue, a reaction between water and halogen-based gas, and particles generated in a measurement unit having a rotary device of the substrate.

Preferably, in a calculation method for calculating a likelihood of the local contact in the peripheral portions of the substrate in the form of a score, the score is calculated based on particle distributions on a surface of portions in contact with other members, which belong to the substrate.

Preferably, in a calculation method for calculating a likelihood of the rubbing between the substrate and the member to surround the corresponding substrate or the particles generated in the member to surround the substrate in the form of a score, the score is calculated based on particle distributions on a surface of the peripheral portions of the substrate.

Preferably, in a calculation method for calculating a likelihood of the gas hole penetration in the form of a score, the score is calculated based on deviation between placement positions of the gas holes of a shower head for supplying a processing gas in each of process modules of the substrate processing system and positions of the particle distributions on the surface of the substrate.

Preferably, in a calculation method for calculating a likelihood of the crystal originated particles in the form of a score, the score is calculated based on particle distributions on a surface at a central portion of the substrate.

Preferably, in a calculation method for calculating a likelihood of the deposited residue in the form of a score, the score is calculated based on the number of particles distributed on a surface at a central portion of the substrate and the number of particles distributed on a surface in the peripheral portions of the substrate.

Preferably, in a calculation method for calculating a likelihood of the reaction between water and halogen-based gas in the form of a score, the score is calculated based on distributions of second degree curves of the particles on the surface of the substrate.

Preferably, in a calculation method for calculating a likelihood of the particles generated in the measurement unit having the rotary device of the substrate in the form of a score, the score is calculated based on spiral distributions of the particles on the surface of the substrate.

Preferably, the user interface device displays the particle distributions on the surface of the substrate and displays a color, shape, size, brightness or display type of the particles pertinent to the respective occurrence factor of particles in the particle distributions differently from a color, shape, size, brightness or display type of the particles pertinent to other remaining occurrence factors of particles, and wherein the display type is either blink or non-blink.

Preferably, the user interface device displays a countermeasure method for each of the occurrence factors of particles.

In accordance with another aspect of the present invention, there is provided a method of determining occurrence factors of particles, comprising: reading a program for executing a calculation method for calculating a likelihood of each of the occurrence factors of particles in the form of a score; calculating the score for each of the occurrence factors of particles based on particle distributions at least on a surface of a substrate using the read program; and displaying the score calculated for each of the occurrence factors of particles.

In accordance with still another aspect of the present invention, there is provided a computer-readable storage medium that stores a program for executing a method of determining occurrence factors of particles in a computer, the method comprising: reading a program for executing a calculation method for calculating a likelihood of each of the occurrence factors of particles in the form of a score; calculating the score for each of the occurrence factors of particles based on particle distributions at least on a surface of a substrate using the read program; and displaying the score calculated for each of the occurrence factors of particles.

In accordance with a system for detecting the occurrence factors of particles according to claim 1, a method of detecting the occurrence factors of particles according to claim 15, and a storage medium according to claim 16, a score for each of the occurrence factors of particles is calculated based on each particle distribution at least on the surface of a substrate using a program for executing a calculation method which calculates a likelihood of each of the occurrence factors of particles in the form of a mask, and the corresponding calculated score is displayed. Accordingly, even a person who has little skill in the occurrence factors of particles can accurately determine the occurrence factors of particles with reference to displayed scores.

In accordance with a system for detecting the occurrence factors of particles according to claim 2, a score is calculated based on at least one of the material, shape, and size of the particles. Accordingly, the score of a likelihood of each of the occurrence factors of particles can be more accurately calculated.

In accordance with a system for detecting the occurrence factors of particles according to claim 3, whether the score of a likelihood of each of the occurrence factors of particles is calculated can be determined depending on the type of substrate processing system using each stored program. Accordingly, the score of a likelihood of the occurrence factor of particles, which cannot be generated, is not calculated, so that the occurrence factors of particles can be accurately determined.

In accordance with a system for detecting the occurrence factors of particles according to claim 4, a program for executing a calculation method which calculates a likelihood of a new occurrence factor of particles in the form of a score can be stored. Accordingly, the occurrence factors of particles can be determined based on information about the latest occurrence factor of particles.

In accordance with a system for detecting the occurrence factors of particles according to claim 6, a score is calculated based on each particle distribution on portions of the surface in contact with other members in a substrate. Particles generated by local contact in the peripheral portions of the substrate chiefly adhere to portions in contact with other members, for example, taper pads in the substrate. Accordingly, a possibility that local contact in the peripheral portions of the substrate may be one of the occurrence factors of particles can be accurately determined.

In accordance with a system for detecting the occurrence factors of particles according to claim 7, a score is calculated based on particle distributions on the surface of the peripheral portions of a substrate. Particles generated by rubbing between the substrate and a member surrounding the corresponding substrate or particles generated in the member surrounding the substrate for the most part adhere to the peripheral portions of the substrate. Accordingly, a possibility that the rubbing between the substrate and the member surrounding the corresponding substrate or the particles generated in the member surrounding the substrate may be one of the occurrence factors of particles can be accurately determined.

In accordance with a system for detecting the occurrence factors of particles according to claim 8, a score is calculated based on deviation between the placement positions of gas holes of a shower head and the positions of particle distributions on the surface of a substrate. Particles generated by the gas hole penetration adhere to the substrate so that the particles correspond to the placement positions of the gas holes of the shower head. Accordingly, the likelihood of the gas hole penetration, which is one of the occurrence factors of particles, can be accurately determined.

In accordance with a system for detecting the occurrence factors of particles according to claim 9, a score is calculated based on particle distributions on a surface at the center of a substrate. Particles generated by COPs are chiefly generated at the center of the substrate. Accordingly, the likelihood of the COPs, which is one of the occurrence factors of particles, can be accurately determined.

In accordance with a system for detecting the occurrence factors of particles according to claim 10, a score is calculated based on the number of particles distributed on a surface at the center of a substrate and based on the number of particles distributed on surfaces in the peripheral portions of the substrate. Accordingly, the likelihood of deposited residue, which is one of the occurrence factors of particles, can be accurately determined.

In accordance with a system for detecting the occurrence factors of particles according to claim 11, a score is calculated based on a distribution of a second degree curve of particles on the surface of a substrate. Particles generated by the reaction between water and halogen-based gas adhere to the substrate in the form of a second degree curve. Accordingly, the likelihood of the reaction between water and halogen-based gas, which is one of the occurrence factors of particles, can be accurately determined.

In accordance with a system for detecting the occurrence factors of particles according to claim 12, a score is calculated based on the spiral distributions of particles on the surface of a substrate. In a measurement unit (for example, a metrology unit) having the rotary device of the substrate, the corresponding substrate is rotated when being tested. Particles generated in the metrology unit adhere in a spiral shape. Accordingly, the likelihood of the particles generated in the measurement unit having the rotary device of the substrate, which is one of the occurrence factors of particles, can be accurately determined.

In accordance with a system for detecting the occurrence factors of particles according to claim 13, in each particle distribution, the color, shape, size, brightness or display type (blink or non-blink) of the particles pertinent to each of the occurrence factors of particles is displayed differently from those of the particles pertinent to other occurrence factors of particles. Accordingly, the clearness of calculated scores can be checked with the naked eye.

In accordance with a system for detecting the occurrence factors of particles according to claim 14, a countermeasure method for each of the occurrence factors of particles is displayed and, therefore, measures can be taken immediately. Accordingly, the time that a substrate processing system takes to stop can be reduced, so that a reduction in the rate of operation of the substrate processing system can be prevented.

BRIEF DESCRIPTION OF THE DRAWINGS

FIGS. 4A and 4B are diagrams showing data used by the system for detecting the occurrence factors of particles of FIG. 3, wherein FIG. 4A shows the image data of a wafer surface and FIG. 4B shows Scanning Electron Microscopy (SEM) image data regarding the size or shape of a particle;

FIGS. 8A and 8B are diagrams showing areas corresponding to taper pads and areas surrounding taper pads on a particle map, wherein FIG. 8A is a plan view showing the positions of the areas corresponding to the taper pads on the particle map, and FIG. 8B is an enlarged plan view showing an area corresponding to each taper pad and an area surrounding the taper pad in the particle map;

FIGS. 10A to 10C are diagrams showing data used to calculate a likelihood of sliding against the focus ring, wherein FIG. 10A is a plan view showing ten evenly divided areas in the peripheral portions of a particle map, FIG. 10B is a graph plotting the number of particles in each of the divided areas of FIG. 10A, and FIG. 10C is a plan view showing edge areas;

FIGS. 14A and 14B are flowcharts showing a likelihood calculation process regarding periphery bias;

FIGS. 20A and 20B are diagrams illustrating the specification of a V-shaped second degree curve at step S1902, wherein FIG. 20A is a plan view showing particle groups in a particle map, and FIG. 20B is a plan view showing a V-shaped second degree curve, which was approximately calculated for the respective particle groups;

FIGS. 22A and 22B are diagrams illustrating the specification of spiral distribution at step S2102, wherein FIG. 22A is a plan view showing the spiral distributions in a particle map, and FIG. 22B is a diagram showing a coordinate system in the case where the x axis denotes a distance from the center of the particle map and the y axis denotes a rotation angle when the center of particles is a rotation center.

DETAILED DESCRIPTION OF THE PREFERRED EMBODIMENTS

Embodiments of the present invention are described below with reference to the accompanying drawings.

Figure 1:
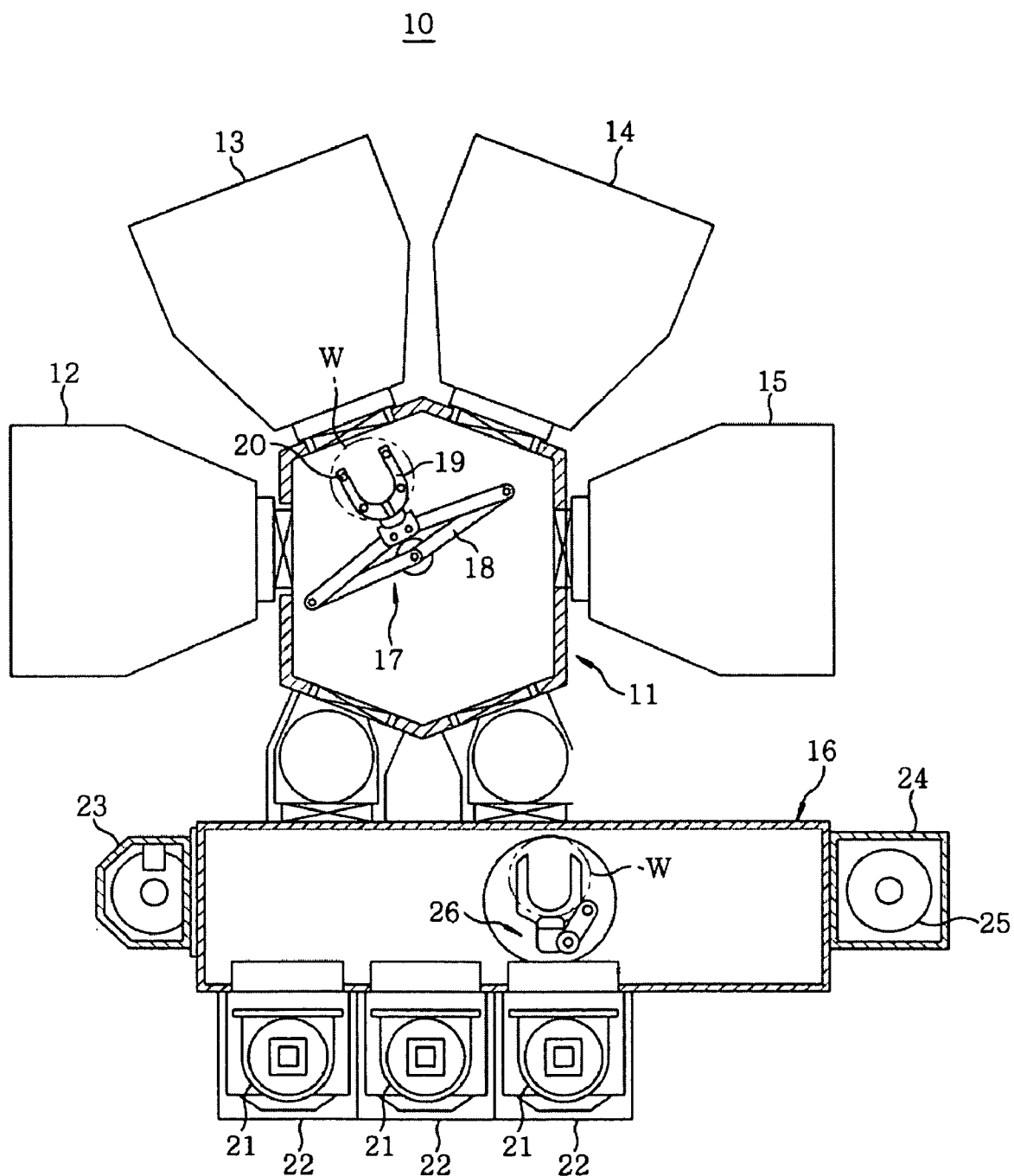
FIG. 1 is a plan view schematically showing the construction of a substrate processing system for processing substrates having adhered particles whose occurrence factors of will be determined using a system for detecting the occurrence factors of particles according to an embodiment of the present invention.

FIG. 1 is a plan view schematically showing the construction of a substrate processing system for processing substrates having adhered particles whose occurrence factors will be determined using a system for detecting the occurrence factors of particles according to an embodiment of the present invention.

In FIG. 1, the substrate processing system 10 includes, when viewed in a plan view, a hexagonal transfer module 11, four process modules 12 to 15 radially arranged around the transfer module 11, and a loader module 16 (that is, a common conveyance chamber having a rectangular shape).

Each of the process modules 12 to 15 is a substrate processing apparatus for performing a specific processing on a substrate for a semiconductor device (hereinafter referred to as a "wafer") W. For example, the process module 12 may be an etching apparatus for performing an etching process on the wafer W using plasma.

In the substrate processing system 10, the internal pressure of the transfer module 11 and each of the process modules 12 to 15 is maintained in a vacuum state, and the internal pressure of the loader module 16 is maintained in an atmospheric pressure state.

The transfer module 11 includes a frog leg-type substrate transfer unit 17, which can be freely bent, stretched and rotated. The substrate transfer unit 17 includes an arm 18 and a transfer fork 19. The arm 18 freely expands or contracts horizontally, and freely rotates. The transfer fork 19 is connected to the front end of the corresponding arm 18 and has a bifurcate shape and supports the wafer W. The substrate transfer unit 17 transfers the wafer W between the respective process modules 12 to 15. Furthermore, the transfer fork 19 includes taper pads 20 (other members) that come into contact with the peripheral portions of the wafer W and have a protrusion shape in order to stabilize the corresponding wafer W.

The loader module 16 is connected to three FOUP mounting tables 22 for enabling respective FOUPs 21, each of which is a container for accommodating wafers W, to be mounted thereon, an orienter 23 for freely aligning the positions of the wafers W taken out of the FOUPs 21, and a metrology unit 24 (a measurement unit) for measuring the surface of the wafer W on which an etching process has been performed. The corresponding metrology unit 24 includes a rotary stand 25 (a rotary tool) configured to enable the wafer W to be mounted thereon and a scanner (not shown) configured to manipulate the surface of the wafer W mounted on the corresponding rotary stand 25. The loader module 16 further includes a substrate transfer unit 26 that is placed therein and configured to convey the wafer W. The loader module 16 conveys the wafer W to a desired position using the corresponding substrate transfer unit 26.

Figure 2:
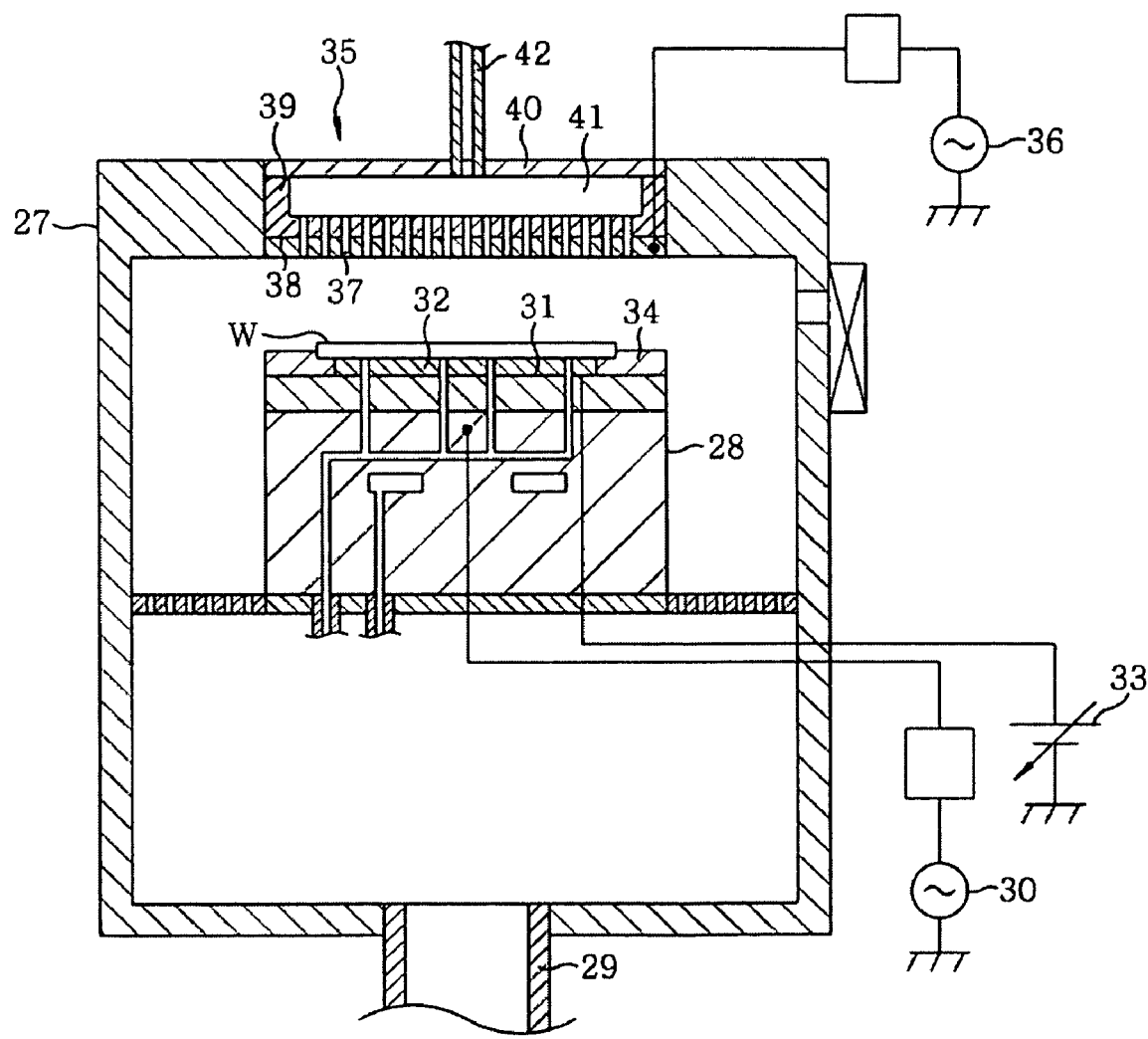
FIG. 2 is a cross-sectional view schematically showing the construction of each of the process modules shown in FIG. 1.

FIG. 2 is a cross-sectional view schematically showing the construction of each of the process modules shown in FIG. 1.

In FIG. 2, the process module 12 includes a chamber 27 configured to accommodate a wafer W having a diameter of, for example, 300 mm and a susceptor 28 configured to have a cylindrical shape and to mount the wafer W thereon within the corresponding chamber 27. An exhaust pipe 29 is further connected to the chamber 27.

A Turbo Molecular Pump (TMP) and a Dry Pump (DP) (all of which are not shown) are connected to the exhaust pipe 29. The pumps exhaust the chamber 27 into a vacuum state, thus reducing the pressure of the chamber.

A lower high frequency power supply 30 is connected to the susceptor 28 within the chamber, and supplies high frequency power to the susceptor 28. An electrostatic chuck 32 in a table form is placed on the upper portion of the susceptor 28. An electrostatic electrode plate 31 is placed within the electrostatic chuck 32. In the electrostatic chuck 32, a DC power supply 33 is electrically connected to the electrostatic electrode plate 31. When positive DC voltage is applied to the electrostatic electrode plate 31, the wafer W is attached to and maintained on the top surface of the electrostatic chuck 32 by Coulombic Force or Johnson-Rahbek Force.

Furthermore, a focus ring 34 (a member surrounding the substrate) having a circular ring shape is placed in the electrostatic chuck 32 so that it surrounds the wafer W that has been attached to and maintained on the top surface of the electrostatic chuck 32. The focus ring 34 is formed of a conductive member, for example, a silicon, and condenses plasma within the chamber 27 on the surface of the wafer W, thereby improving the efficiency of the etching process.

A shower head 35 is placed on the ceiling of the chamber 27 to be opposite the susceptor 28. An upper high frequency power supply 36 is connected to the shower head 35. The upper high frequency power supply 36 supplies high frequency power to the shower head 35. The shower head 35 includes a ceiling electrode plate 38 having a number of gas holes 37 and a circular plate shape, a cooling plate 39 for supporting the corresponding ceiling electrode plate 38, and a cover 40 for covering the corresponding cooling plate 39. A buffer chamber 41 is further provided within the corresponding cooling plate 39. A processing gas inlet pipe 42 is connected to the buffer chamber 41. The shower head 35 supplies a processing gas (for example, a mixed gas including a CF-based gas), supplied from the processing gas inlet pipe 42 to the buffer chamber 41, into the chamber 27 via the gas holes 37. In the ceiling electrode plate 38, the gas holes 37 are formed through the bottom thereof in contact with the inside of the chamber 27 in a regular arrangement, for example, in a radial or concentric circular arrangement.

In the process module 12, a processing gas is supplied to the inside of the chamber 27 and the susceptor 28 or the shower head 35 applies high frequency voltage to the inside of the chamber 27, so that plasma is generated from the processing gas. An etching process is performed on the wafer W using the corresponding plasma.

A system for detecting the occurrence factors of particles according to the present embodiment is described below.

Figure 3:
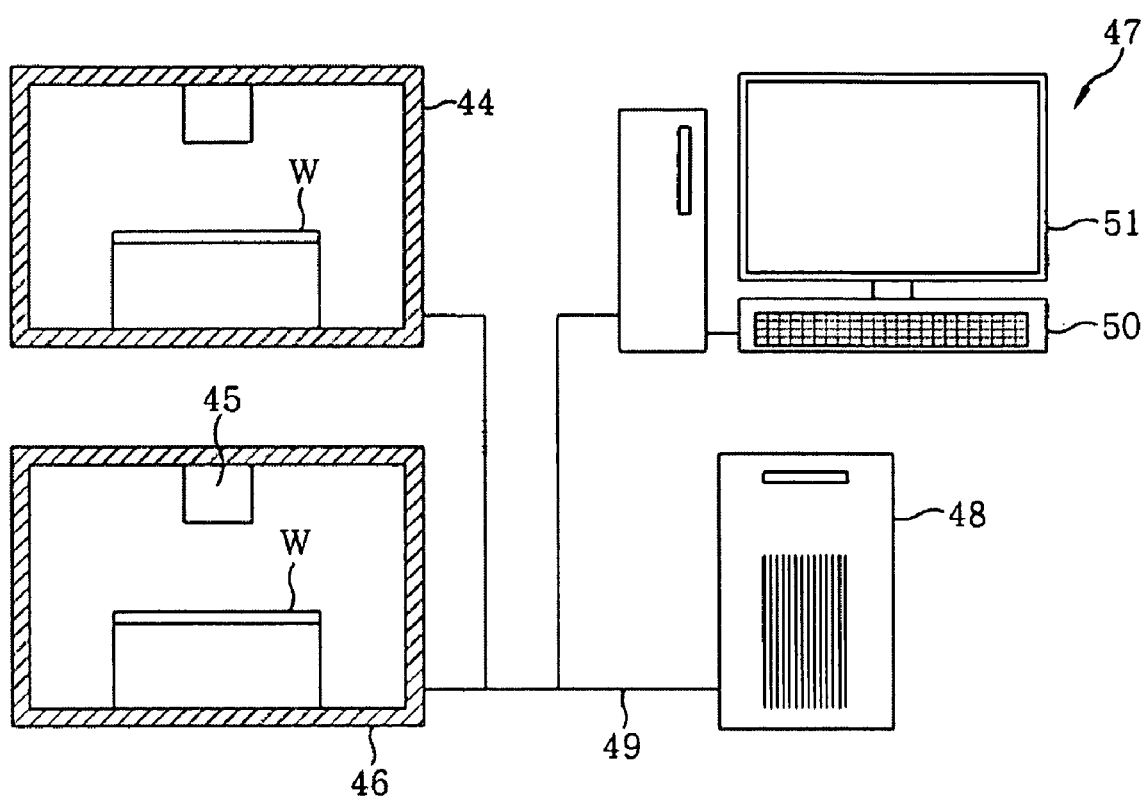
FIG. 3 is a diagram schematically showing the construction of the system for detecting the occurrence factors of particles according to the present embodiment.

FIG. 3 is a diagram schematically showing the construction of the system for detecting the occurrence factors of particles according to the present embodiment.

Figure 4A:
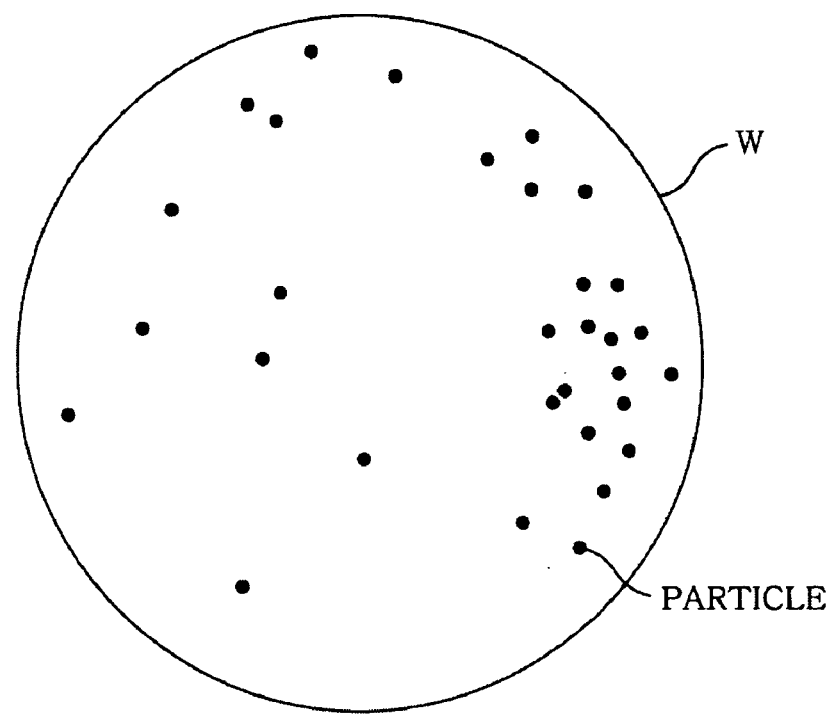
Figure 4B:
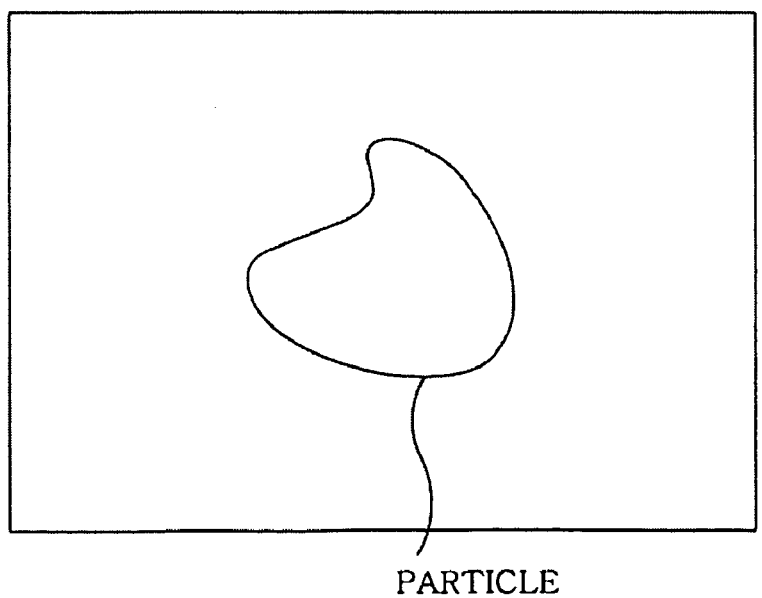

In FIG. 3, the system for detecting the occurrence factors of particles 43 includes a wafer surface inspection apparatus 44 configured to acquire the image data (FIG. 4A) of a wafer (W) surface by photographing the surface of the wafer W or receiving reflected light from the surface of the wafer W, a particle material analysis device 46 configured to include a Scanning Electron Microscopy (SEM)-Energy Dispersive X-ray (SEM-EDX) device 45, to obtain the size or shape (FIG. 4B) of each particle on the surface of the wafer W in the form of SEM image data, and to analyze the material of the corresponding particle, a client PC 47 configured to function as a user interface device, a host server 48 configured to function as an apparatus for detecting the occurrence factors of particles, and a cable 49 configured to connect the wafer surface inspection apparatus 44, the particle material analysis device 46, the client PC 47 and the host server 48 to one another so that they can communicate between themselves.

The client PC 47 includes a keyboard 50 for receiving input from a customer's technician and a display 51 for displaying respective likelihoods regarding the occurrence factors of particles. The host server 48 includes memory (a storage unit) and a Central Processing Unit (CPU) (a calculation unit) (all of which are not shown).

In the case where particles adhere to the surface of the wafer W, the memory of the host server 48 stores a program for executing a likelihood calculation method of calculating, in connection with each of the occurrence factors of particles, a clearness score (a possibility) (hereinafter referred to as a "likelihood") regarding which of the occurrence factors has generated the particles. The corresponding memory further previously has stored the representative materials (sodium, sulfur, aluminum, fluorine, carbon, etc.), shapes (a spherical shape, a bunch shape, a film shape, a needle shape, a quadrangular pyramid shape, a watermark shape, a flower petal shape, a flake shape, etc.) and sizes of the respective particles generated by the occurrence factors of particles.

The CPU of the host server 48 converts the image data of a wafer (W) surface, transmitted by the wafer surface inspection apparatus 44, into a particle map (that is, data indicative of the distributions of particles on the surface of the wafer W) through binary conversion, etc. based on the specification values of the wafer (the size of the outer or inner circumferential circle of the wafer W), reads a program for executing a likelihood calculation method regarding each of the occurrence factors of particles from the memory, and calculates a likelihood of each of the occurrence factors of particles using the read program for executing the likelihood calculation method based on the particle map or the data of the materials, shapes and sizes of the particles transmitted by the particle material analysis device 46. In the present embodiment, the image data of the surface of a wafer W having a diameter of 300 mm is converted into a particle map having a diameter of 600 mm.

In the present embodiment, the memory of the host server 48 stores programs for executing respective likelihood calculation methods corresponding to contact with taper pads (local contact at the peripheral portions of a substrate), sliding against the focus ring (rubbing between a substrate and a member surrounding the substrate), an attacked shoulder of the focus ring (particles generated in the member surrounding the substrate), the gas hole penetration, periphery bias, COPs, deposited residue, the reaction between water and CF-based gas (the reaction between water and halogen-based gas), and particles generated in the metrology unit (particles generated in the measurement unit having the rotary device of the substrate). Respective occurrence factors of particles will be described later. Furthermore, the corresponding memory does not need to store all of the above programs for executing the likelihood calculation methods, and may store programs for executing likelihood calculation methods other than the above programs for executing the likelihood calculation methods. Moreover, the programs for executing the likelihood calculation methods may be freely deleted from or added to the memory. For example, if a new occurrence factor of particles is found, a new program for executing a likelihood calculation method corresponding to the occurrence factor of particles may be added. The new program for executing the likelihood calculation method may be supplied to a storage medium or to memory via a network.

Furthermore, the system for detecting the occurrence factors of particles 43 may not include the wafer surface inspection apparatus 44 and the particle material analysis device 46. In this case, a particle map or the data of the material, shape, and size of each particle may be input via the client PC 47.

Figure 5:
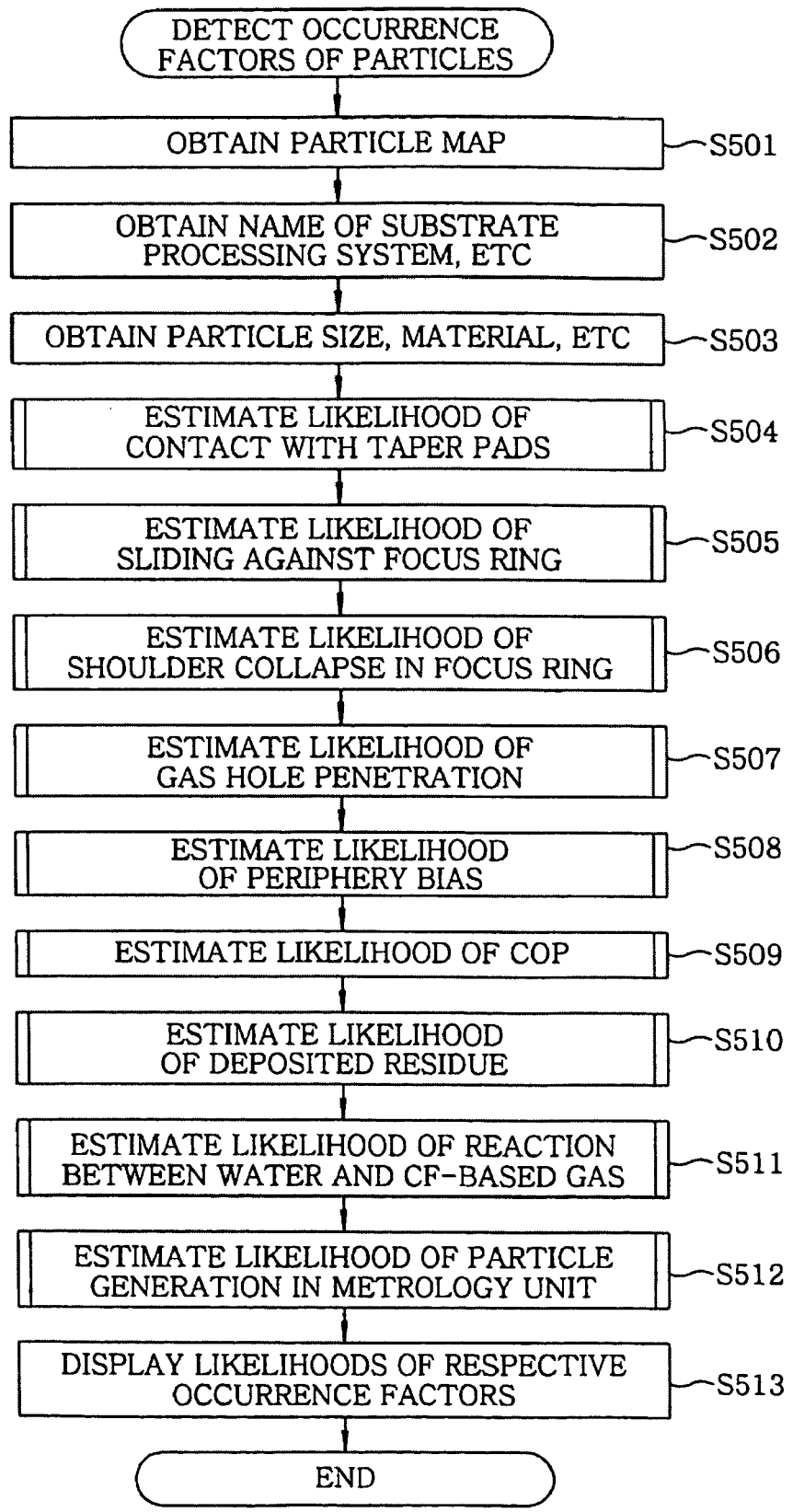
FIG. 5 is a flowchart showing a process of detecting the occurrence factors of particles in a method of detecting the occurrence factors of particles according to the present embodiment.

FIG. 5 is a flowchart showing a process of detecting the occurrence factors of particles in a method of detecting the occurrence factors of particles according to the present embodiment. This processing is executed by the CPU of the host server 48 in response to the input of a customer's technician through the client PC 47.

In FIG. 5, a particle map is first acquired by converting the image data of a wafer (W) surface, transmitted by the wafer surface inspection apparatus 44, into the particle map at step S501. The name of the substrate processing system 10 or the process module 12, which has been input by a customer's technician through the client PC 47, is acquired from the corresponding client PC 47 at step S502. The data of the material, shape, and size of each particle is then acquired from the particle material analysis device 46 at step S503.

A program for executing a likelihood calculation method regarding contact with taper pads (that is, one of the occurrence factors of particles) is then read from the memory. A likelihood of contact with taper pads is calculated based on the particle map or the data of the material, shape, and size of each particle using the read program for executing the likelihood calculation method at step S504. In a similar way, a likelihood of sliding against the focus ring is calculated at step S505, a likelihood of the attacked shoulder of the focus ring is calculated at step S506, a likelihood of the gas hole penetration is calculated at step S507, a likelihood of periphery bias is calculated at step S508, a likelihood of COPs is calculated at step S509, a likelihood of deposited residue is calculated at step S510, a likelihood of the reaction between water and CF-based gas is calculated at step S511, and a likelihood of particles generated in the metrology unit is calculated at step S512.

The calculated likelihoods regarding the respective occurrence factors of particles are displayed on the display 51 at step S513, and this process is then terminated.

Figure 6:
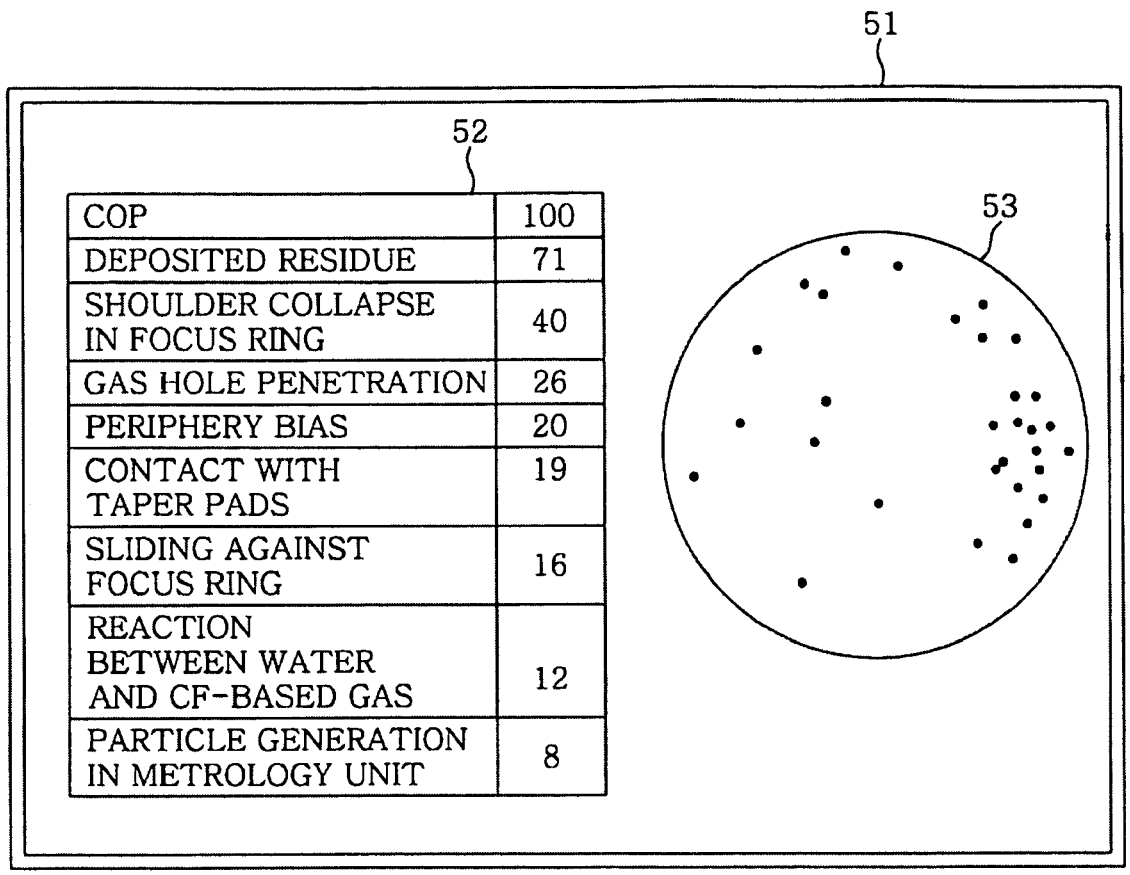
FIG. 6 is a diagram showing content displayed on the display of a client PC at step S513 of FIG. 5.

FIG. 6 is a diagram showing content displayed on the display of the client PC at step S513 of FIG. 5.

In FIG. 6, the display 51 displays a particle map 53 and a likelihood list 52 showing the respective likelihoods regarding the occurrence factors of particles. In the likelihood list 52, the occurrence factors of particles are arranged in descending order of likelihoods, and the corresponding likelihoods for the respective occurrence factors of particles are displayed. The particle map 53 shows the distributions of all particles having specific or higher sizes on the wafer (W) surface. However, if a specific occurrence factor of particles is indicated in the likelihood list 52 using a pointing device, etc., the color, shape, size, brightness and display type (blink or non-blink) of each of the particles pertinent to the indicated occurrence factor of particles may be displayed differently from those of each of the particles pertinent to the remaining occurrence factors of particles in the particle map 53.

Furthermore, if a specific occurrence factor of particles is selected from the likelihood list 52 by double clicking the specific occurrence factor of particles using a pointing device or the like, a countermeasure method for the selected occurrence factor of particles (for example, the exchange of the focus ring 34 or the cleaning of the shower head 35) may be displayed as text.

In the processing of FIG. 6, the respective likelihoods regarding the occurrence factors of particles are displayed. Accordingly, even a customer's technician may accurately determine the occurrence factors of particles with reference to the displayed likelihoods.

Furthermore, in the processing of FIG. 6, a likelihood is calculated based on a particle map or the material, shape, and size of a particle. Accordingly, respective likelihoods regarding the occurrence factors of particles can be more accurately calculated. In addition, a likelihood of each of the occurrence factors of particles need not be calculated based on all of a particle map and the material, shape and size of particles. In the case where any one piece of data regarding the particle map, and the material, shape or size of the particles is omitted, a likelihood of each of the occurrence factors of particles may be calculated based on only the remaining data.

In the above-described system 43, the memory of the host server 48 may store a new program for executing a likelihood calculation method corresponding to a new occurrence factor of particles. Accordingly, a customer's technician may determine the occurrence factors of particles based on information about the latest occurrence factors of particles.

Furthermore, on the display 51 of the client PC 47, the color, shape, size, brightness and display type (blink or non-blink) of each of the particles pertinent to each of the occurrence factors of particles are displayed differently from those of each of the particles pertinent to the remaining occurrence factors of particles in the particle map 53. Accordingly, the clearness of each likelihood pertinent to each of the calculated occurrence factors of particles may be checked with the naked eye.

Furthermore, since a countermeasure method for a selected occurrence factor of particles is displayed on the display 51 of the client PC 47, measurements can be immediately taken. Accordingly, the time that the substrate processing system 10 takes to stop may be shortened. Consequently, a reduction in the rate of operation of the substrate processing system 10 can be prevented.

Although in the above-described system 43, the client PC 47 and the host server 48 are constructed separately, the client PC and the host server may be integrated into a single unit. Furthermore, the integrated client PC and host server may be attached to the substrate processing system 10.

The calculation of the likelihoods at steps S504 to S512 of FIG. 5 is described below.

Figure 7:
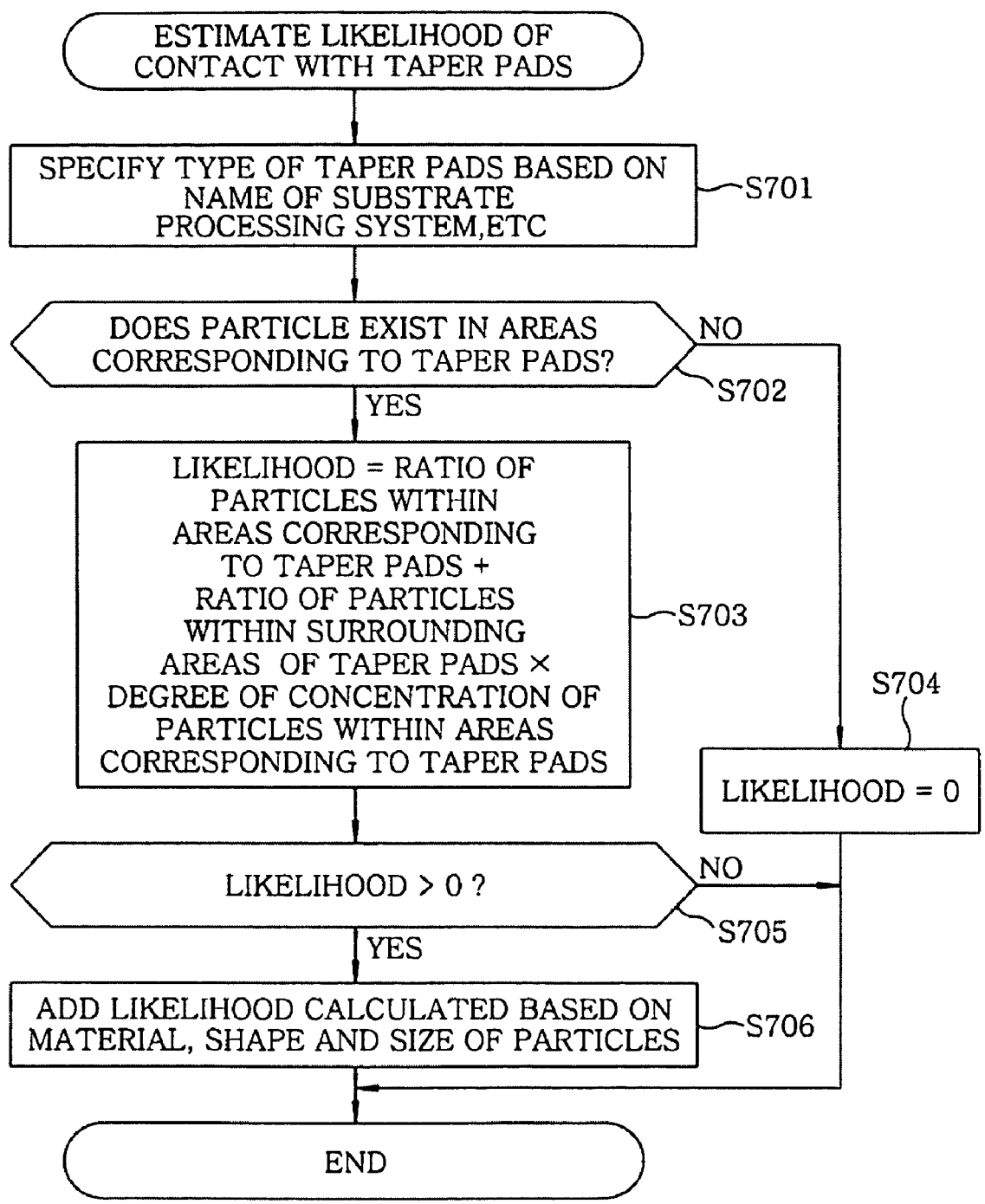
FIG. 7 is a flowchart showing a likelihood calculation process regarding contact with a taper pad.

FIG. 7 is a flowchart showing a likelihood calculation process regarding contact with taper pads at step S504 of FIG. 5. Particles generated by contact between the taper pads 20 and the wafer W adhere for the most part to portions in contact with the taper pads 20, which belong to the wafer W. Accordingly, in the processing of FIG. 7, a likelihood is calculated based on the distribution density of particles at the portions in contact with the taper pads 20, which belong to the wafer W.

In FIG. 7, first, the shape of the transfer fork 19 or the placement positions of the taper pads 20 or the number of placement positions of the taper pads 20 on the transfer fork 19 may differ depending on the type of substrate processing system 10 or the process module 12. Accordingly, the type (placement positions and the number of placement positions) of the taper pads 20 is specified based on the name of the substrate processing system 10, etc., which is acquired from the client PC 47 at step S701.

The portions of the wafer W in contact with the taper pads 20 are then specified based on the specified placement positions or the number of placement positions of the taper pads 20. Areas corresponding to the specified contact portions in the particle map are defined as areas 54 corresponding to the taper pads. It is then determined whether particles exist in the areas 54 corresponding to the taper pads at step S702.

Figure 8A:
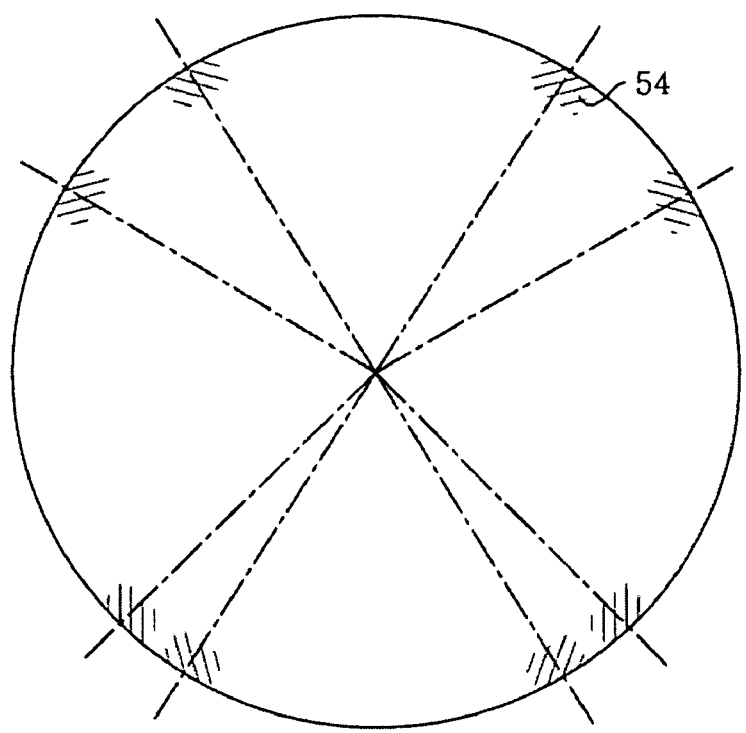

As indicated by a corresponding shaded portion of FIG. 8A, each of the areas 54 corresponding to the taper pads is the area of the particle map that ranges over a rotation angle of ±5° (in the case where the center of the particle map is a rotation center) around a portion in contact with the taper pad 20 and extends 30 mm from the circumference of the particle map toward the center of the particle map. FIG. 8A also corresponds to the case where the transfer fork 19 has eight taper pads 20.

Figure 8B:
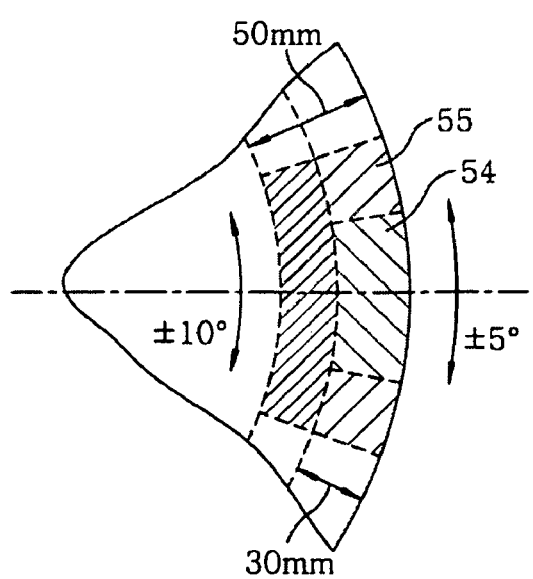

If, as a result of the determination at step S702, the particles are determined to have existed in the areas 54 corresponding to the taper pads, the ratio of particles within the areas corresponding to the taper pads, the ratio of particles within the surrounding areas of the taper pads, and the degree of concentration of the particles within the areas corresponding to the taper pads are calculated based on the particle map. The surrounding areas 55 of the taper pads are areas surrounding the respective areas 54 corresponding to the taper pads. Each of the surrounding areas 55 of the taper pads is an area of the particle map, which extends ±10° in a rotation angle around a portion in contact with each of the taper pads 20 in the case where the center of the particle map is a rotation center and extends 50 mm from the circumference of the particle map to the center of the particle map. In this case, the area 54 corresponding to the taper pad is excluded from the corresponding area (refer to FIG. 8B).

The ratio of particles within the areas corresponding to the taper pads, the ratio of particles within the surrounding areas of the taper pads, and the degree of concentration of particles within the areas corresponding to the taper pads are respectively expressed by the following equations:

The ratio of particles within the areas corresponding to the taper pads=the distribution density of particles within the areas 54 corresponding to the taper pads/the distribution density of particles in the area between the radii 200 mm and 300 mm (outside) in the particle map The ratio of particles within the surrounding areas of the taper pads=the distribution density of particles within the surrounding areas 55 of the taper pads/the distribution density of particles in the area between the radii 200 mm and 300 mm (outside) in the particle map The degree of concentration of particles within the areas corresponding to the taper pads=the number of particles within the areas 54 corresponding to the taper pads/(the number of particles within the areas 54 corresponding to the taper pads+the number of particles within the surrounding areas 55 of the taper pads)×100

A likelihood of contact with taper pads is calculated using the following equation at step S703, and the process proceeds to step S705.

Likelihood=the ratio of particles within the areas corresponding to the taper pads+the ratio of particles within the surrounding areas of the taper pads× the degree of concentration of particles within the areas corresponding to the taper pads It is determined whether the calculated likelihood is more than 0 at step S705. If, as a result of the determination at step S705, the calculated likelihood is determined to be 0, the process is terminated. If, as a result of the determination at step S705, the calculated likelihood is determined to be more than 0, the likelihood calculated based on the material, shape and size of the particles is added to the calculated likelihood at step S706, and the process is terminated.

At step S706, the data of the representative materials, shapes and sizes of the particles, which have been generated by contact with taper pads and stored in memory, is compared with data of the materials, shapes and sizes of particles which have been acquired from the particle material analysis device 46. If, as a result of the comparison, they have a degree of similarity to the materials or there is a degree of coincidence in the shapes and sizes, a possibility that contact with taper pads will be one of the occurrence factors of particles is determined to be high, so the likelihood is calculated as 5. A likelihood for each of the materials, shapes, and sizes is also calculated.

If, as a result of the determination at step S702, the particles are determined not to have existed in the areas 54 corresponding to the taper pads, a likelihood of the contact with taper pads is set to 0 at step S704, and the process is terminated.

According to the processing of FIG. 7, a likelihood is calculated based on the distribution density of particles within the portions of the wafer W in contact with the taper pads 20. Accordingly, a likelihood about whether particles have been generated by contact between the taper pads 20 and the wafer W can be accurately calculated. Consequently, a possibility that the contact with the taper pads may be one of the occurrence factors of particles can be accurately determined.

Figure 9:
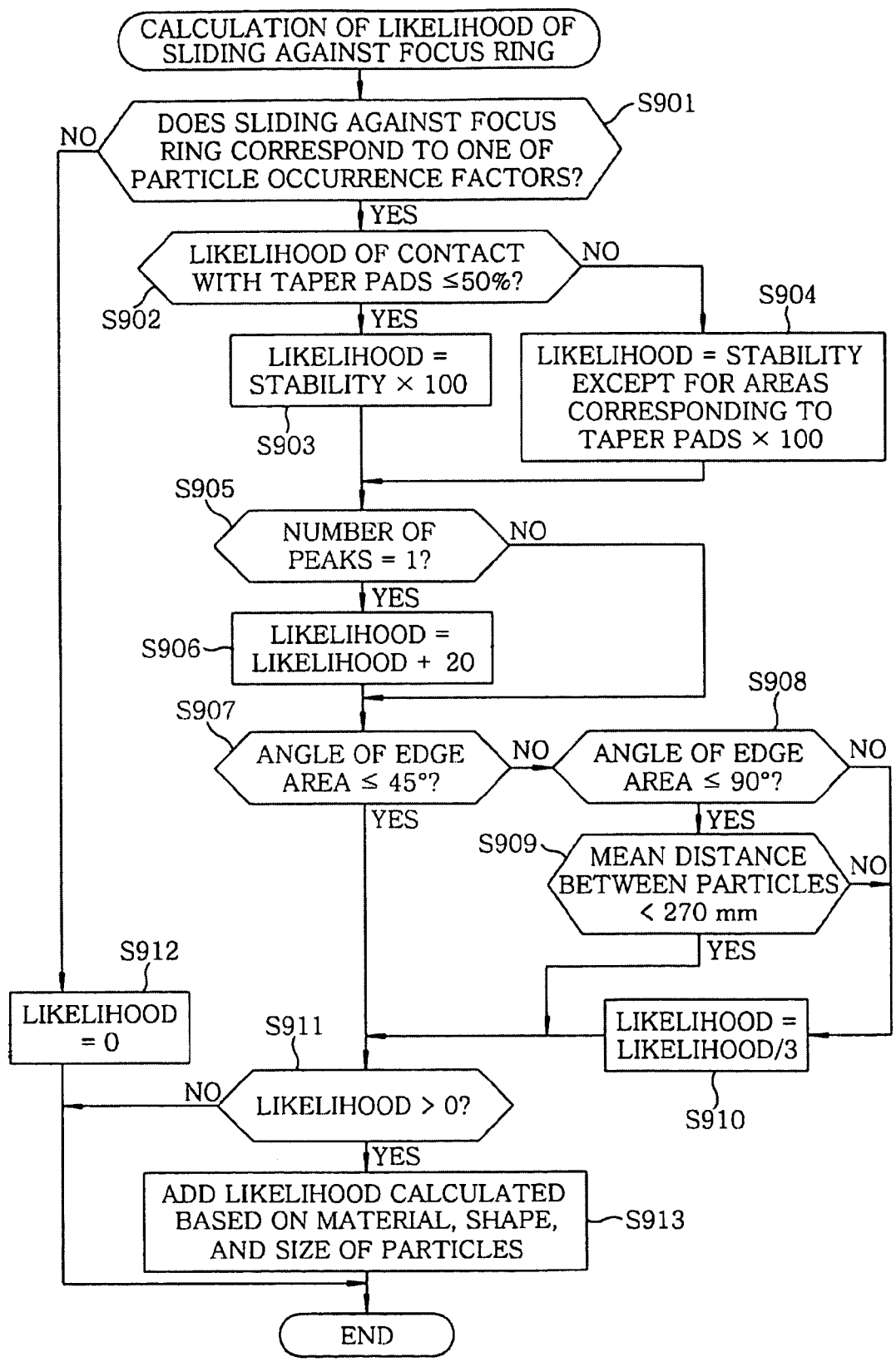
FIG. 9 is a flowchart showing a likelihood calculation process regarding sliding against a focus ring.

FIG. 9 is a flowchart showing a likelihood calculation process regarding sliding against the focus ring at step S505 of FIG. 5. Particles generated by rubbing between the focus ring 34 and the wafer W chiefly adhere to the peripheral portions of the wafer W. Rubbing is a phenomenon in which the wafer W locally comes into contact with the focus ring 34. Accordingly, particles are locally distributed in the peripheral portions of the wafer W and are also distributed in relatively inside portions. Consequently, in the processing of FIG. 9, a likelihood is calculated based on the distribution density of particles in the peripheral portions of the wafer W.

The type of the focus ring 34 may differ depending on the type of the substrate processing system 10 or the process module 12, and rubbing between the focus ring 34 and the wafer W may not be generated depending on the type of the substrate processing system 10. For this reason, in FIG. 9, it is first determined whether sliding against the focus ring is one of the occurrence factors of particles based on the name of the substrate processing system 10, which has been acquired from the client PC 47, at step S901.

If, as a result of the determination at step S901, the sliding against the focus ring is determined to be one of the occurrence factors of particles, it is determined that a likelihood of the contact with taper pads is 50 or less at step S902.

If, as a result of the determination at step S902, the likelihood of the contact with taper pads is determined to be 50 or less, a likelihood is calculated using the following equation at step S903, and the process proceeds to step S905.

Likelihood=stability×100

Here, the stability is calculated using the following equation:

Stability=vector mean/scalar mean

Here, the vector mean is the mean value of the distances from the center of the particle map to all particles existing in the area outside a radius of 250 mm in the particle map. The scalar mean is the distance from a coordinate origin to a point corresponding to an average x component and an average y component obtained from the respective x and y components of the position vectors of all the particles existing in the area outside a radius of 250 mm in the particle map in the case where the center of the particle map is the coordinate origin.

If, as a result of the determination at step S902, the likelihood of the contact with taper pads is determined to be more than 50, a likelihood is calculated using the following equation at step S904, and the process proceeds to step S905.

Likelihood=stability in the case where the areas corresponding to the taper pads are excluded×100

The stability in the case where the areas corresponding to the taper pads are excluded is stability regarding all particles existing in the area which is the area outside a radius of 250 mm or more in the particle map and from which the areas corresponding to the taper pads are excluded. The stability is also calculated using the above equation.

It is then determined whether the number of peaks in the peripheral portion of the wafer W is 1 at step S905. Here, in the case where an area having a radius of 200 mm or more in the particle map is divided into ten equal areas in a circumferential direction (FIG. 10A) and the numbers of particles existing in the respective areas (1, 2, 3, . . . , and 10) are plotted on a graph (FIG. 10B), if on the corresponding graph, a difference between the number of particles existing in a specific area and the number of particles existing in neighboring areas is greater than a standard deviation of the number of particles existing in the entire area, the corresponding specific area is referred to as the above peak (in FIG. 10B, the area 9 corresponds to the peak).

If, as a result of the determination at step S905, the number of peaks is determined to be 1, 20 is added to the calculated likelihood at step S906, and the process proceeds to step S907. If, as a result of the determination at step S905, the number of peaks is determined not to be 1, the process proceeds to step S907 without change.

It is then determined whether or not the angle of an edge area is 45° or less at step S907. If, as a result of the determination at step S907, the angle of the edge area is 45° or less, the process proceeds to step S911. If, as a result of the determination at step S907, the angle of the edge area is greater than 45°, the process proceeds to step S908.

Here, the edge area is an area (corresponding to a dark portion in FIG. 10C) in which 90% or more of all particles existing in a corresponding area are distributed. The edge area belongs to the area between two valleys (the area 7 and the area 4) including the peak (the area 9) therebetween in FIG. 10B.

It is determined whether or not the angle of the edge area is 90° or less at step S908. If, as a result of the determination at step S908, the angle of the edge area is determined to be 90° or less, it is determined whether the average of the distances from the center of the particle map to all particles existing in an area having a radius of 200 mm or more in the particle map (hereinafter referred to as a "particle average distance") is shorter than 270 mm at step S909. If, as a result of the determination at step S909, the particle average distance is determined to be shorter than 270 mm, the process proceeds to step S911.

If, as a result of the determination at step S908, the angle of the edge area is determined to be greater than 90°, and if, as a result of the determination at step S909, the particle average distance is determined to be greater than 270 mm, the calculated likelihood is divided by 3 at step S910, and the process proceeds to step S911.

It is then determined whether the calculated likelihood is more than 0 at step S911. If, as a result of the determination at step S911, the calculated likelihood is determined to be 0, the process is terminated. If, as a result of the determination at step S911, the calculated likelihood is determined to be more than 0, the likelihood of a corresponding one of the occurrence factors of particles, which has been calculated based on the material, shape and size of the particles, is added to the corresponding likelihood, as in step S706, at step S913, and the process is terminated.

Meanwhile, if, as a result of the determination at step S901, the sliding against the focus ring is determined not to be one of the occurrence factors of particles, a likelihood of the sliding against the focus ring is set to 0 at step S912, and the process is terminated.

Since in accordance with the processing of FIG. 9, a likelihood is calculated based on the distribution density of particles in the peripheral portions of the wafer W, a likelihood about whether particles have been generated by rubbing between the focus ring 34 and the wafer W can be accurately calculated. As a result, a possibility that the sliding against the focus ring may be one of the occurrence factors of particles can be accurately determined.

Figure 11:
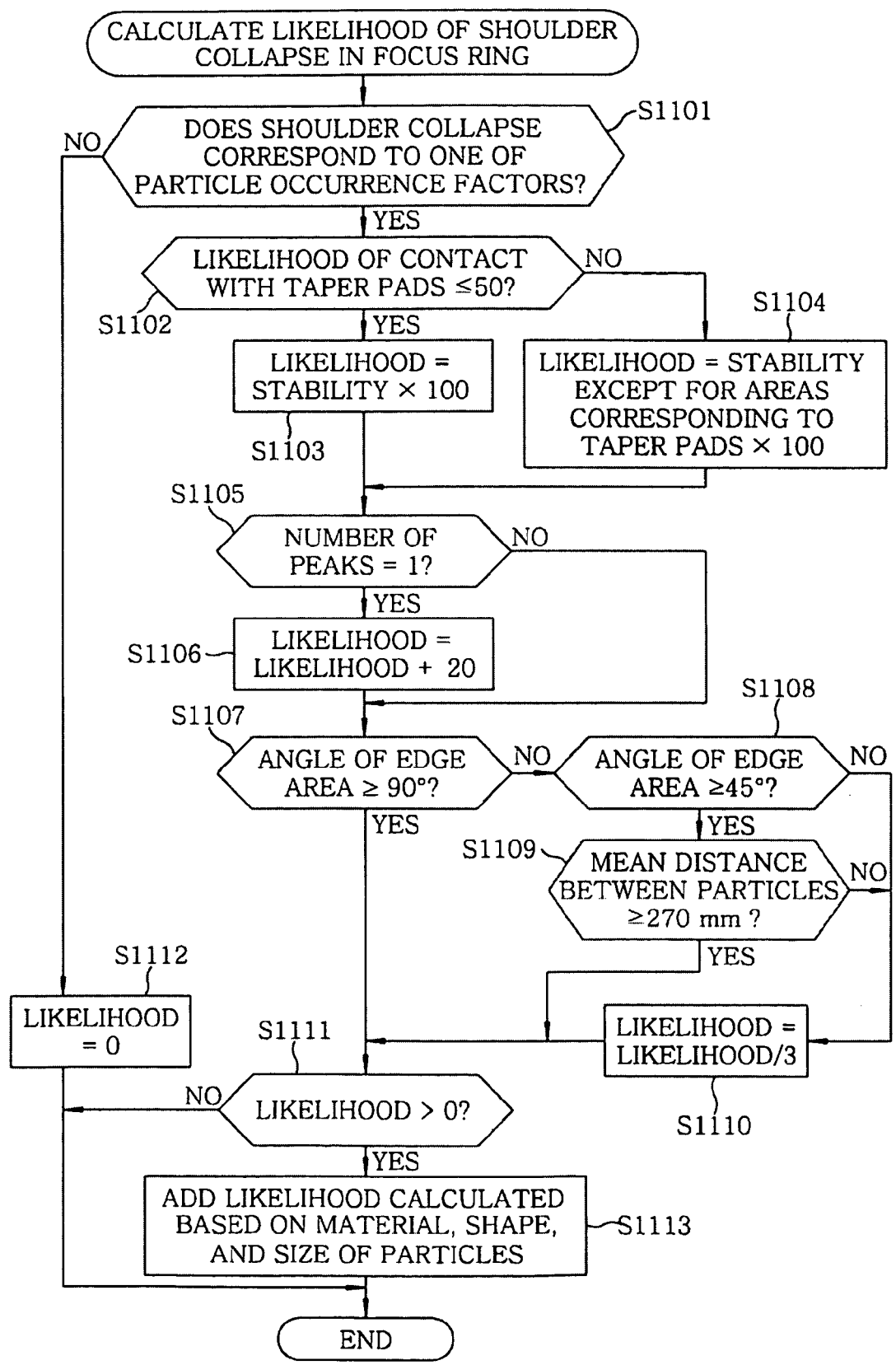
FIG. 11 is a flowchart showing a likelihood calculation process regarding an attacked shoulder of the focus ring.

FIG. 11 is a flowchart showing a likelihood calculation process regarding an attacked shoulder of the focus ring at step S506 of FIG. 5. Particles generated by the attacked shoulder of the focus ring 34 by the wafer W chiefly adhere to the peripheral portions of the wafer W. The attacked shoulder is a phenomenon in which the shoulder portions of the focus ring are peeled off by the sputtering of ions existing in plasma. Thus, the particles are widely distributed in the peripheral portions of the wafer W, and are distributed in relatively outside areas. Accordingly, in the processing of FIG. 11, a likelihood is calculated based on the distribution density of particles in the peripheral portions of the wafer W.

In this case, the attacked shoulder of the focus ring 34 by the wafer W may not be generated depending on the type of the substrate processing system 10. For this reason, in FIG. 11, it is first determined whether the attacked shoulder of the focus ring is one of the occurrence factors of particles based on the name of the substrate processing system 10, which has been acquired from the client PC 47, at step S1101.

If, as a result of the determination at step S1101, the attacked shoulder of the focus ring is determined to be one of the occurrence factors of particles, it is determined whether a likelihood of contact with taper pads is 50 or less at step S1102.

If, as a result of the determination at step S1102, the likelihood of the contact with taper pads is determined to be 50 or less, a likelihood of the attacked shoulder of the focus ring is calculated using the following equation at step S1103, and the process proceeds to step S1105. Here, stability is equal to the stability in the processing of FIG. 9.

Likelihood=stability×100

If, as a result of the determination at step S1102, the likelihood of the contact with taper pads is determined to be more than 50, a likelihood of the attacked shoulder of the focus ring is calculated using the following equation at step S1104, and the process proceeds to step S1105.

Likelihood=stability in the case where the areas corresponding to the taper pads are excluded×100

In this case, the stability in the case where the areas corresponding to the taper pads are excluded also is equal to the stability in the case where the areas corresponding to the taper pads are excluded in the processing of FIG. 9.

It is then determined whether the number of peaks in the peripheral portions of the wafer W is 1 at step S1105. Here, the peak is also equal to the peak in the processing of FIG. 9.

If, as a result of the determination at step S1105, the number of peaks is determined to be 1, 20 is added to the calculated likelihood at step S1106, and the process proceeds to step S1107. If, as a result of the determination at step S1105, the number of peaks is determined not to be 1, the process proceeds to step S1107 without change.

It is then determined whether or not the angle of an edge area is 90° or more at step S1107. If, as a result of the determination at step S1107, the angle of the edge area is determined to be 90° or more, the process proceeds to step S1111. If, as a result of the determination at step S1107, the angle of the edge area is determined to be greater than 90°, the process proceeds to step S1108. Here, the edge area is also equal to the edge area in the processing of FIG. 9.

It is then determined whether the angle of the edge area is 45° or more at step S1108. If, as a result of the determination at step S1108, the angle of the edge area is determined to be 45° or more, it is determined whether the above-described particle average distance is 270 mm or more at step S1109. If, as a result of the determination at step S1109, the particle average distance is determined to be 270 mm or more, the process proceeds to step S1111.

If, as a result of the determination at step S1108, the angle of the edge area is determined to be less than 45°, and if, as a result of the determination at step S1109, the particle average distance is determined to be less than 270 mm, the calculated likelihood is divided by 3 at step S1110, and the process proceeds to step S1111.

It is then determined whether the calculated likelihood is more than 0 at step S1111. If, as a result of the determination at step S1111, the calculated likelihood is determined to be 0, the process is terminated. If, as a result of the determination at step S1111, the calculated likelihood is determined to be more than 0, the likelihood of a corresponding one of the occurrence factors of particles, which has been calculated based on the material, shape and size of the particles, is added to the calculated likelihood, as in step S706, at step S1113, and the process is terminated.

Meanwhile, if, as a result of the determination at step S1101, the attacked shoulder of the focus ring is determined not to be one of the occurrence factors of particles, a likelihood of the attacked shoulder of the focus ring is set to 0 at step S1112, and the process is terminated.

In accordance with the processing of FIG. 11, a likelihood is calculated based on the distribution density of particles in the peripheral portions of the wafer W. Accordingly, a likelihood about whether particles have been generated by the attacked shoulder of the focus ring 34 can be accurately calculated. As a result, a possibility that the attacked shoulder of the focus ring may be one of the occurrence factors of particles can be accurately determined.

Figure 12:
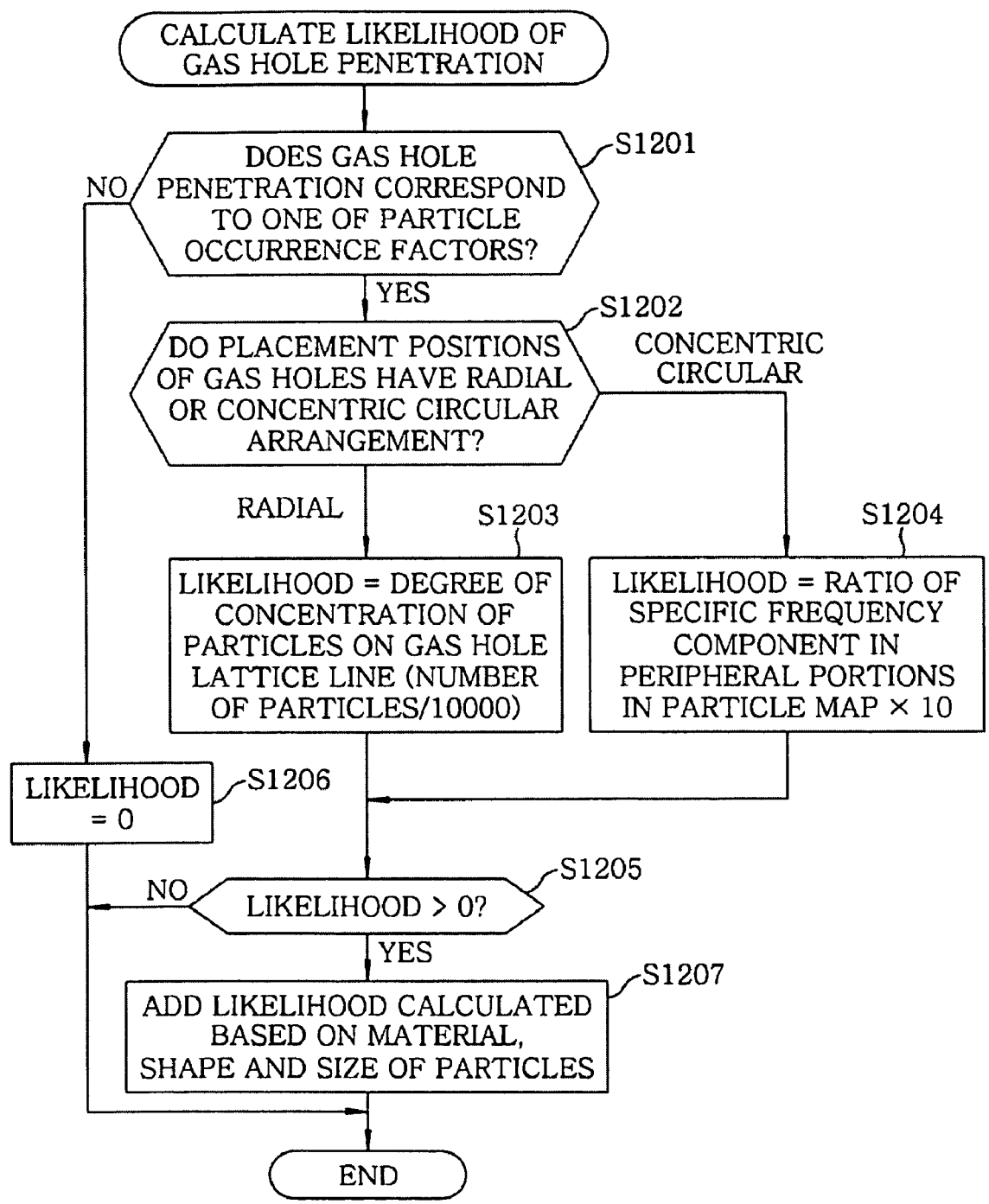
FIG. 12 is a flowchart showing a likelihood calculation process the regarding gas hole penetration.

FIG. 12 is a flowchart showing a likelihood calculation process regarding the gas hole penetration at step S507 of FIG. 5. The gas hole penetration is a phenomenon in which particles generated on the upper portion within the chamber 27 are carried up to the surface of the wafer W by the viscous flow of a processing gas discharged from the respective gas holes 37 of the shower head 35 and the corresponding particles adhere to the surface of the wafer W. For this reason, the particles generated through the gas hole penetration adhere to the wafer W, for example, in a radial or concentric circular shape so that the particles correspond to the placement positions of the gas holes 37 in the shower head 35. Accordingly, in the processing of FIG. 12, a likelihood is calculated based on deviation between the placement positions of the gas holes 37 of the shower head 35 and the distribution positions of particles on the surface of the wafer W.

Here, the gas hole penetration may not be generated depending on the type of the substrate processing system 10. For this reason, in FIG. 12, it is first determined whether the gas hole penetration is one of the occurrence factors of particles based on the name of the substrate processing system 10, which has been acquired from the client PC 47, at step S1201.

If, as a result of the determination at step S1201, the gas hole penetration is determined to be one of the occurrence factors of particles, it is determined whether the placement positions of the gas holes 37 in the shower head 35 have a radial or concentric circular shape based on the name of the substrate processing system 10 at step S1202.

If, as a result of the determination at step S1202, the placement positions of the gas holes 37 in the shower head 35 is determined to have the radial shape, a likelihood of the gas hole penetration is calculated using the following equation at step S1203, and the process proceeds to step S1205.

Likelihood=the degree of concentration of particles toward a gas hole lattice line×(the number of particles/10000)

In this case, the degree of concentration of particles toward the gas hole lattice line is calculated using the following equation:

The degree of concentration of particles in gas hole lattice line=2500−(standard deviation of (distance from the gas hole lattice line )²

Here, the distance from the gas hole lattice line is the minimum of the mean values of distances from each of the particles, which are included in each mesh when lattices, each formed of meshes having one side in the range of 20 to 40 mm, overlap each other in the particle map and the corresponding lattices deviate from each other, to each side (line) of the corresponding mesh. Furthermore, a distance from each of the particles to each side of the mesh has a relative value that is obtained when the length of each side of the corresponding mesh is 100.

If, as a result of the determination at step S1202, the placement positions of the gas holes 37 are determined to have a concentric circular shape, a likelihood of the gas hole penetration is calculated using the following equation at step S1204, and the process proceeds to step S1205.

Likelihood=the ratio of a frequency component in the peripheral portions of the particle map×10

Figure 13:
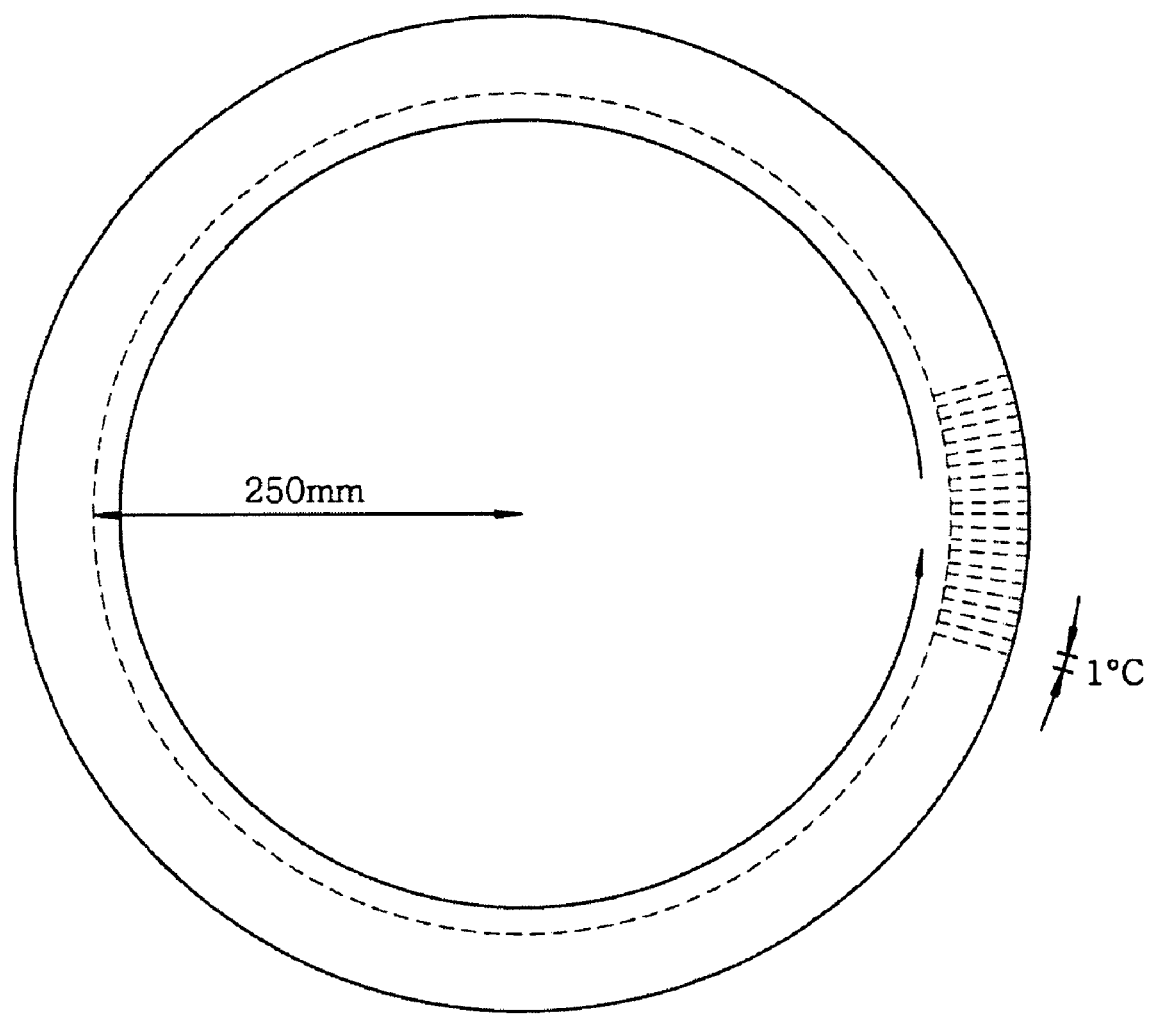
FIG. 13 is a plan view showing areas used to calculate the ratio of a specific frequency component in the peripheral portions of a particle map.

In this case, the ratio of a specific frequency component in the peripheral portions of the particle map is the ratio of a frequency component in the range of 130 to 150 that is obtained using a band pass filter. Here, the frequency component in the range of 130 to 150 is obtained based on a sequence of numbers including the number of particles which are included in each of divided areas (see FIG. 13) when the area outside a radius of 250 mm in the particle map is divided at every 1° with the center of the corresponding particle map set to a rotation center.

It is then determined whether the calculated likelihood is more than 0 at step S1205. If, as a result of the determination at step S1205, the calculated likelihood is determined to be 0, the process is terminated. If, as a result of the determination at step S1205, the calculated likelihood is determined to be more than 0, the likelihood of a corresponding one of the occurrence factors of particles, which has been calculated based on the material, shape and size of the particles, is added to the calculated likelihood, as in step S706, at step S1207, and the process is terminated.

Meanwhile, if, as a result of the determination at step S1201, the gas hole penetration is determined not to be one of the occurrence factors of particles, a likelihood of the gas hole penetration is set to 0 at step S1206, and the process is terminated.

In accordance with the processing of FIG. 12, a likelihood is calculated based on deviation between the placement positions of the gas holes 37 in the shower head 35 and the distribution positions of particles on the surface of the wafer W. Accordingly, a likelihood about whether particles have been generated by the gas hole penetration can be accurately calculated. As a result, a possibility that the gas hole penetration may be one of the occurrence factors of particles can be accurately determined.

Figure 14A:
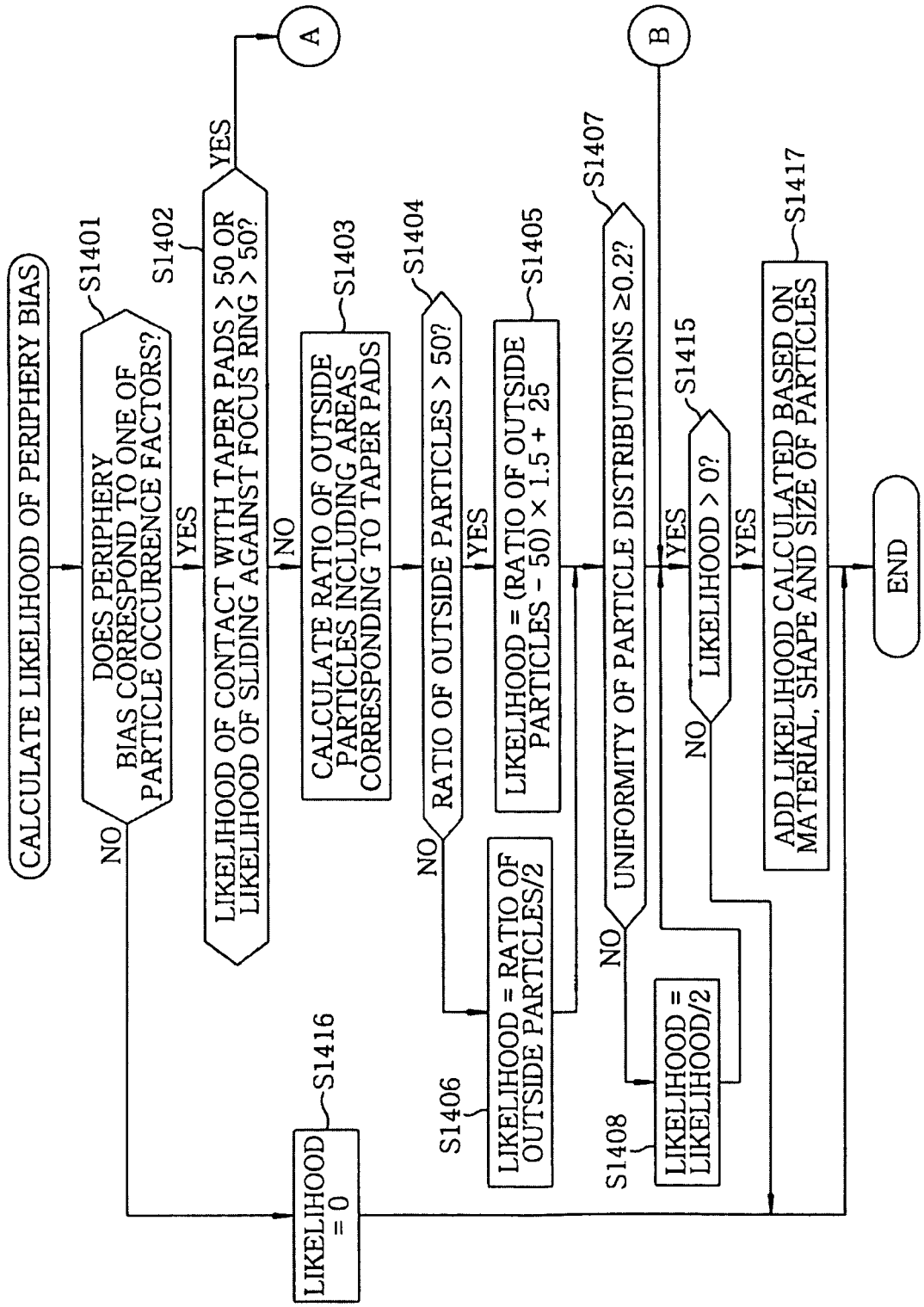

FIGS. 14A and 14B are flowcharts showing a likelihood calculation process regarding periphery bias at step S508 of FIG. 5. The periphery bias corresponds to the situation in which numerous particles are distributed in the peripheral portions of the wafer W. Accordingly, in the processing of FIGS. 14A and 14B, a likelihood is calculated based on the ratio of particles existing in the peripheral portions of the wafer W.

Here, the periphery bias may not be generated depending on the type of the substrate processing system 10. For this reason, in FIGS. 14A and 14B, it is first determined whether the periphery bias is one of the occurrence factors of particles based on the name of the substrate processing system 10, which has been acquired from the client PC 47, at step S1401.

If, as a result of the determination at step S1401, the periphery bias is determined to be one of the occurrence factors of particles, it is determined whether a likelihood of contact with taper pads is more than 50 or a likelihood of sliding against the focus ring is more than 50 at step S1402.

Figure 10A:
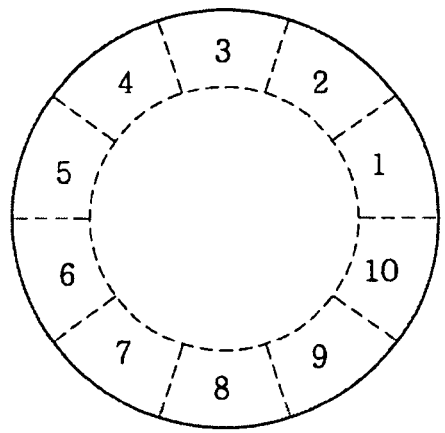
Figure 10B:
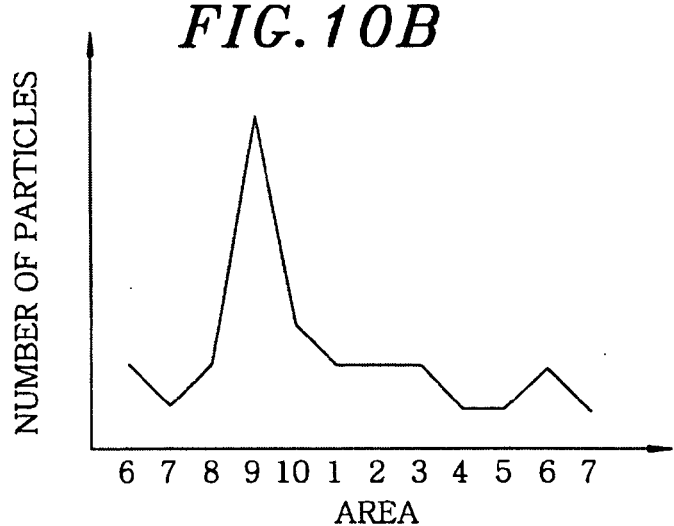
Figure 10C:
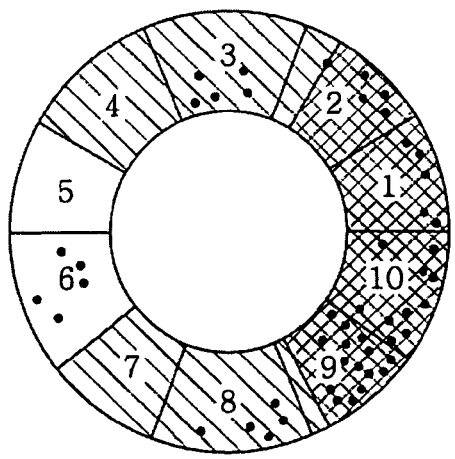

If, as a result of the determination at step S1402, the likelihood of contact with taper pads is determined to be 50 or less or the likelihood of sliding against the focus ring is determined to be 50 or less, the ratio of outside particles, including the areas corresponding to the taper pads of FIG. 10A, is calculated using the following equation at step S1403.

The ratio of outside particles=the number of particles per unit area in the area having a radius of 200 mm or more in the particle map/the number of particles per unit area in the entire area of the particle map×100

It is then determined whether the ratio of the outside particles is more than 50 at step S1404. If, as a result of the determination at step S1404, the ratio of the outside particles is determined to be more than 50, a likelihood of the periphery bias is calculated using the following equation at step S1405, and the process proceeds to step S1407.

Likelihood=(the ratio of outside particles−50)×1.5+25

If, as a result of the determination at step S1404, the ratio of the outside particles is determined to be 50 or less, a likelihood of the periphery bias is calculated using the following equation at step S1406, and the process proceeds to step S1407.

Likelihood=the ratio of outside particles/2

Figure 15:
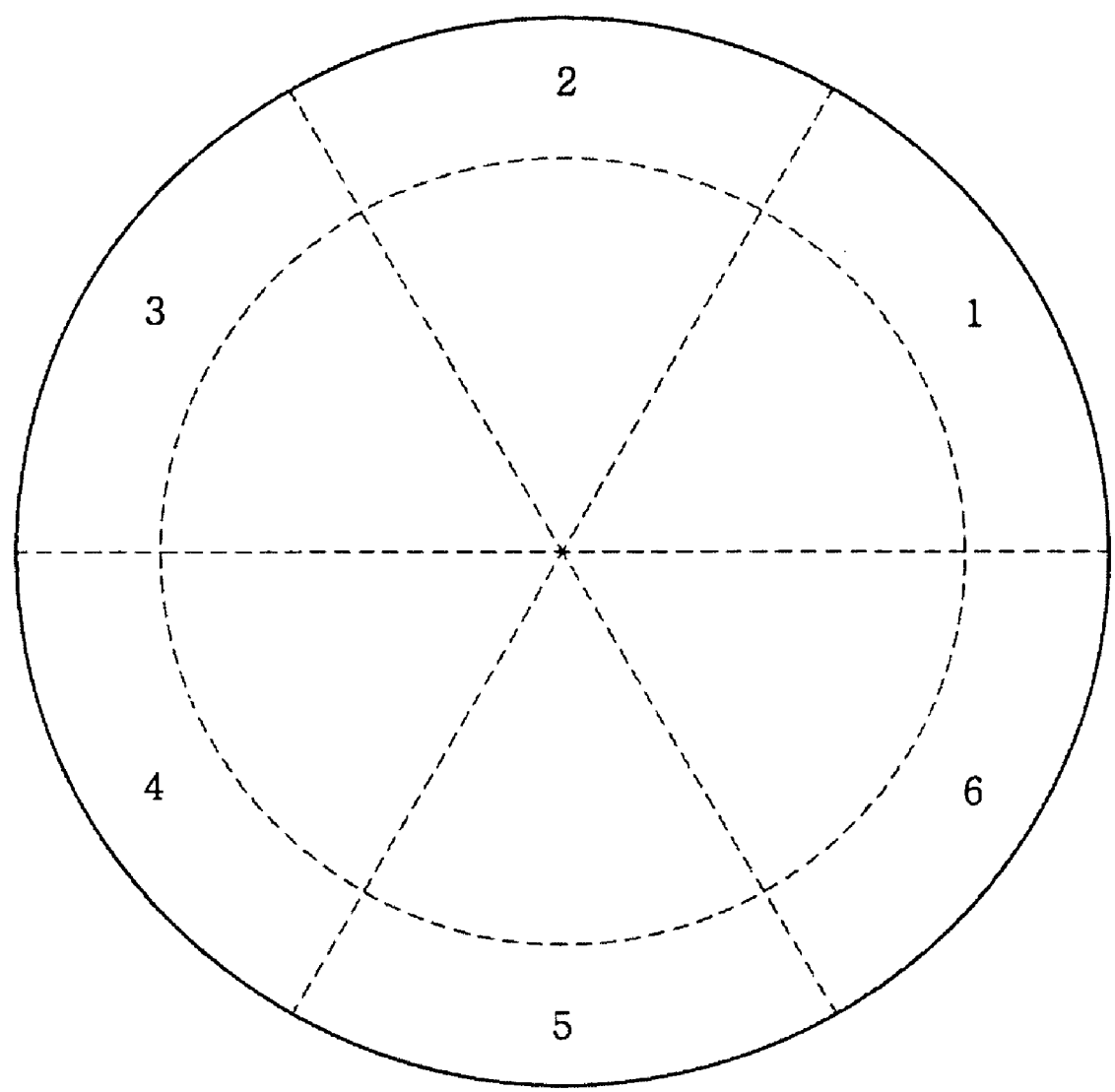
FIG. 15 is a plan view showing six evenly-divided areas in the peripheral portions of a particle map.

It is then determined whether the uniformity of a particle distribution is 0.2 or more at step S1407. Here, the uniformity of the particle distribution refers to a value in which, in the case where the area having a radius of 200 mm or more in the particle map is divided into six equal areas in a circumferential direction (FIG. 15), the minimum of the numbers of particles in the six respective divided areas, is divided by the maximum of the numbers of particles in the six respective divided areas.

If, as a result of the determination at step S1407, the uniformity of the particle distribution is determined to be 0.2 or more, the process proceeds to step S1415 without change. If, as a result of the determination at step S1407, the uniformity of the particle distribution is determined to be less than 0.2, the calculated likelihood is divided by 2 at step S1408, and the process proceeds to step S1415.

If, as a result of the determination at step S1402, the likelihood of contact with taper pads is determined to be more than 50 or the likelihood of sliding against the focus ring is determined to be more than 50, the ratio of outside particles other than the areas corresponding to the taper pads of FIG. 10A is calculated at step S1409.

It is then determined whether the ratio of the outside particles is more than 50 at step S1410. If, as a result of the determination at step S1410, the ratio of the outside particles is determined to be more than 50, a likelihood of the periphery bias is calculated using the following equation at step S1411, and the process proceeds to step S1413.

Likelihood=(the ratio of outside particles−50)×1.5+25

If, as a result of the determination at step S1410, the ratio of the outside particles is determined to be 50 or less, a likelihood of the periphery bias is calculated using the following equation at step S1412, and the process proceeds to step S1413.

Likelihood=the ratio of outside particles/2

It is then determined whether the uniformity of the particle distribution is 0.1 or more at step S1413.

If, as a result of the determination at step S1413, the uniformity of the particle distribution is determined to be 0.1 or more, the process proceeds to step S1415 without change. If, as a result of the determination at step S1413, the uniformity of the particle distribution is determined to be less than 0.1, the likelihood is divided by 2 at step S1414, and the process proceeds to step S1415.

It is then determined whether the calculated likelihood is more than 0 at step S1415. If, as a result of the determination at step S1415, the calculated likelihood is determined to be 0, the process is terminated. If, as a result of the determination at step S1415, the calculated likelihood is determined to be more than 0, the likelihood of a corresponding one of the occurrence factors of particles, which has been calculated based on the material, shape and size of the particles, is added to the calculated likelihood, as in step S706, at step S1417, and the process is terminated.

Meanwhile, if, as a result of the determination at step S1401, the periphery bias is determined not to be one of the occurrence factors of particles, a likelihood of the periphery bias is set to 0 at step S1416, and the process is terminated.

In accordance with the processing of FIGS. 14A and 14B, a likelihood is calculated based on the ratio of particles (the ratio of outside particles) existing in the peripheral portions of the wafer W. Accordingly, a likelihood about whether the particles have been generated by the periphery bias can be accurately calculated.

Figure 16:
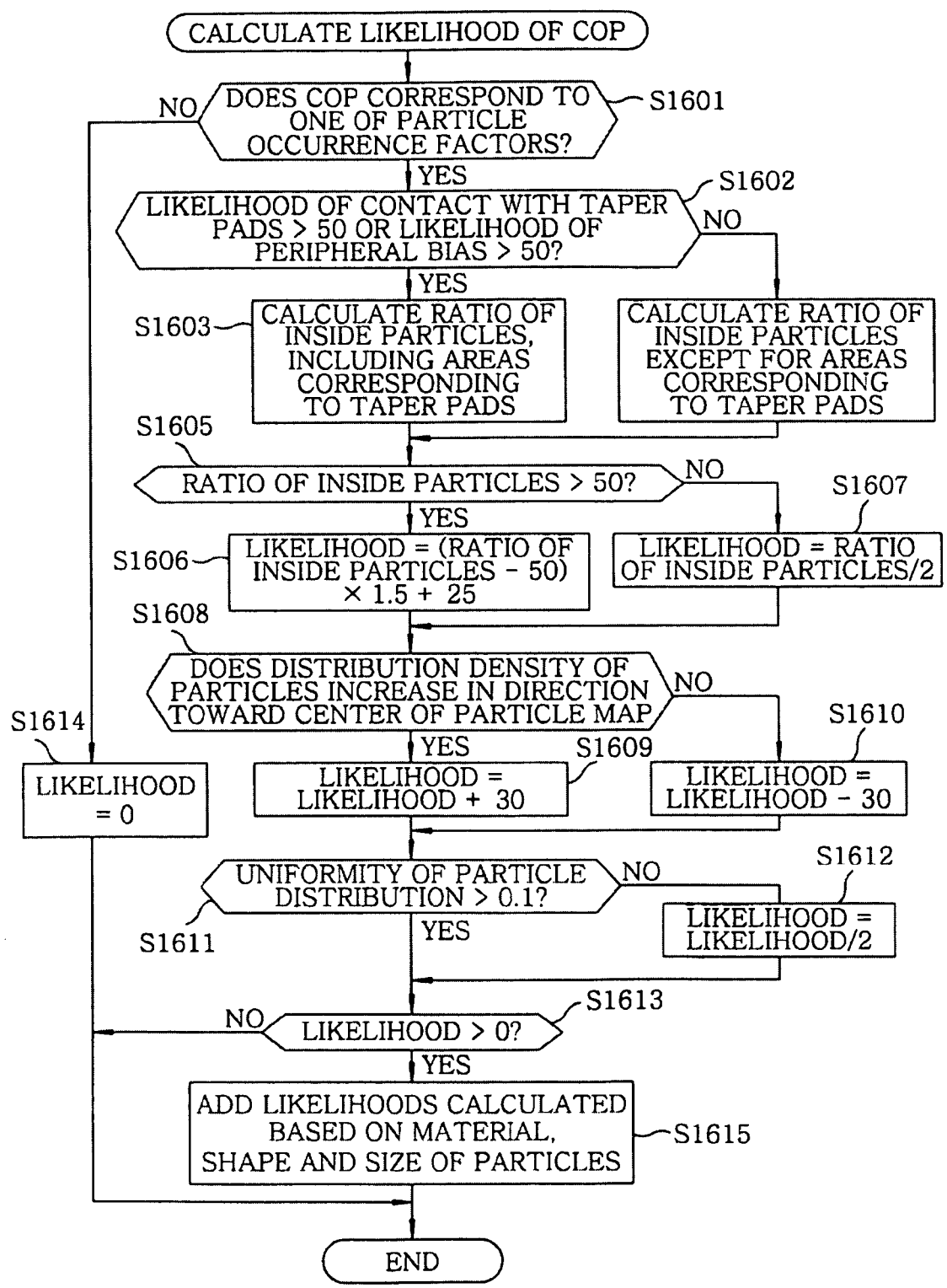
FIG. 16 is a flowchart showing a likelihood calculation process regarding Crystal-originated Particles (COPs)

FIG. 16 is a flowchart showing a likelihood calculation process regarding COPs at step S509 of FIG. 5. The COPs are particles generated by the crystal defects of the wafer W, but are not particles adhering to the outside of the wafer W. Furthermore, the crystal defects are chiefly generated at the center of the ingot of silicon from which a wafer is cut out when the ingot is manufactured. As a result, particles caused by COPs are likely to occur at the center of the wafer W. Accordingly, in the processing of FIG. 16, a likelihood is calculated based on the distribution density of particles on the surface at the center of the wafer W.

Here, the COPs may not be generated depending on the type of a wafer. Furthermore, a wafer to be used is approximately determined depending on the type of the substrate processing system 10. Accordingly, in the processing of FIG. 16, it is first determined whether the COPs correspond to one of the occurrence factors of particles based on the name of the substrate processing system 10, which has been acquired from the client PC 47, at step S1601.

If, as a result of the determination at step S1601, the COPs are determined to be one of the occurrence factors of particles, it is determined whether a likelihood of contact with taper pads is more than 50 or a likelihood of periphery bias is more than 50 at step S1602.

If, as a result of the determination at step S1602, the likelihood of the contact with taper pads is determined to be more than 50 or the likelihood of the periphery bias is determined to be more than 50, the ratio of inside particles, including the areas corresponding to the taper pads of FIG. 10A, is calculated using the following equation at step S1603.

The ratio of inside particles=the number of particles per unit area in the area having a radius of 200 mm or less in the particle map/the number of particles per unit area in the entire area of the particle map×100

If, as a result of the determination at step S1602, the likelihood of the contact with taper pads is determined to be 50 or less or the likelihood of the periphery bias is determined to be 50 or less, the ratio of inside particles other than the areas corresponding to the taper pads of FIG. 10A is calculated at step S1604.

It is then determined whether the ratio of the inside particles is more than 50 at step S1605. If, as a result of the determination at step S1605, the ratio of the inside particles is determined to be more than 50, a likelihood is calculated using the following equation at step S1606, and the process proceeds to step S1608.

Likelihood=(the ratio of inside particles−50)×1.5+25

If, as a result of the determination at step S1605, the ratio of the inside particles is determined to be 50 or less, a likelihood is calculated using the following equation at step S1607, and the process proceeds to step S1608.

Likelihood=the ratio of inside particles/2

Figure 17:
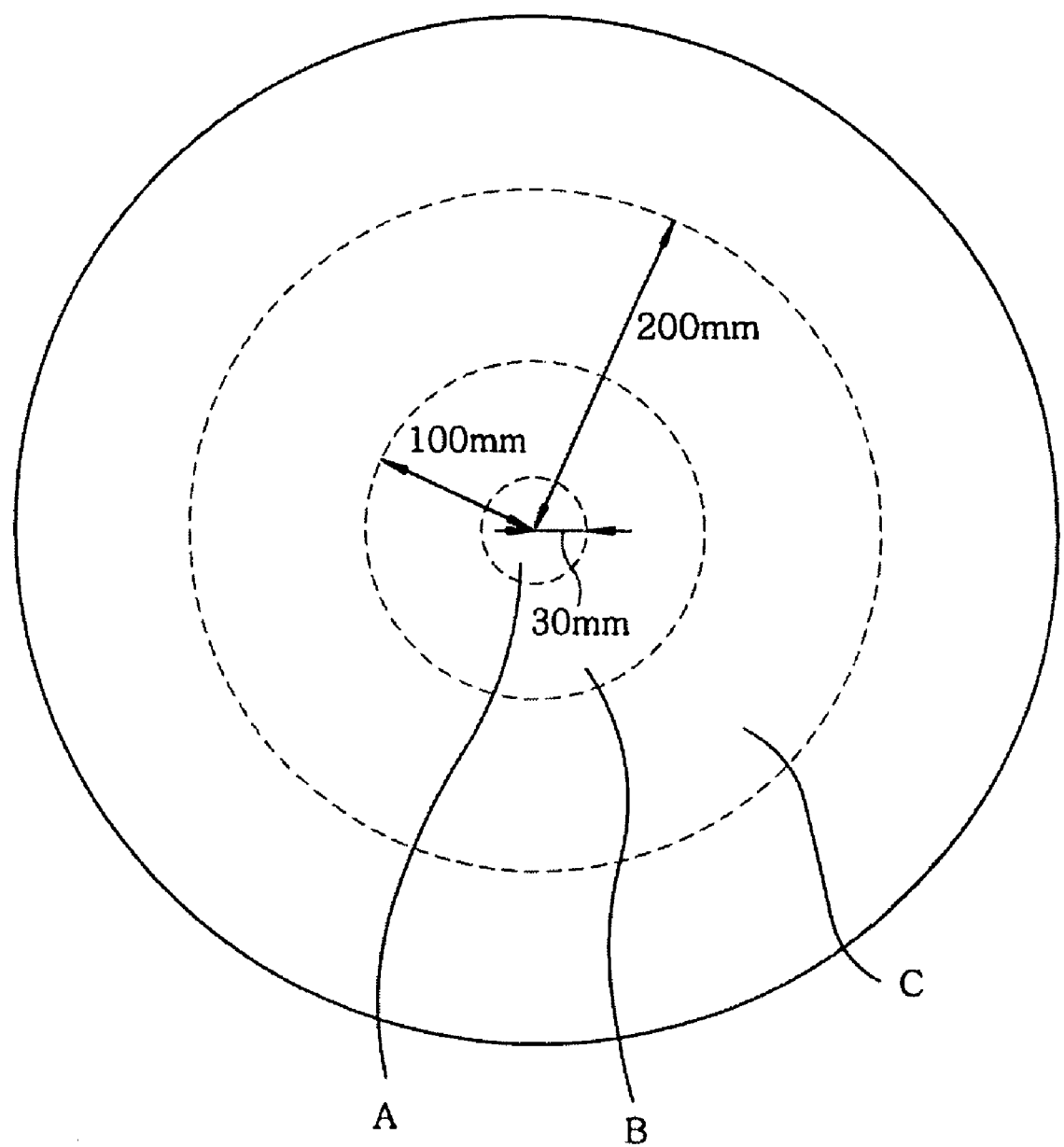
FIG. 17 is a plan view showing areas divided on the basis of the center of a particle map.

It is then determined whether the distribution density of the particles increases in the direction toward the center of the particle map at step S1608. In more detail, as shown in FIG. 17, the numbers of particles per unit area in an area (an area A) inside a radius of 30 mm, an area (an area B) between a radius of 30 mm and a radius of 100 mm and an area (an area C) outside a radius of 200 mm in the particle map are calculated. It is then determined whether the numbers of particles per unit area fulfill the number in the area A≧the number in the area B≧the number in the area C.

If, as a result of the determination at step S1608, the distribution density of the particles is determined to increase in the direction toward the center of the particle map, 30 is added to the calculated likelihood at step S1609. If, as a result of the determination at step S1608, the distribution density of the particles is determined not to increase in the direction toward the center of the particle map, 30 is subtracted from the calculated likelihood at step S1610.

It is then determined whether the uniformity of a particle distribution is more than 0.1 at step S1611. Here, the uniformity of the particle distribution is equal to the uniformity of the particle distribution in the processing of FIGS. 14A and 14B.

If, as a result of the determination at step S1611, the uniformity of the particle distribution is determined to be more than 0.1, the process proceeds to step S1613 without change. If, as a result of the determination at step S1611, the uniformity of the particle distribution is determined to be 0.1 or less, the calculated likelihood is divided by 2 at step S1612, and the process proceeds to step S1613.

It is then determined whether the calculated likelihood is more than 0 at step S1613. If, as a result of the determination at step S1613, the calculated likelihood is determined to be 0, the process is terminated. If, as a result of the determination at step S1613, the calculated likelihood is determined to be more than 0, the likelihood of a corresponding one of the occurrence factors of particles, which has been calculated based on the material, shape and size of the particles, is added to the calculated likelihood, as in step S706, at step S1615, and the process is terminated.

Meanwhile, if, as a result of the determination at step S1601, the COPs are determined not to be one of the occurrence factors of particles, a likelihood of the COPs is set to 0 at step S1614, and the process is terminated.

In accordance with the processing of FIG. 16, a likelihood is calculated based on the distribution density of particles on the surface at the center of the wafer W. Accordingly, a likelihood about whether particles have been generated by COPs can be accurately calculated. As a result, a possibility that the COPs may be one of the occurrence factors of particles can be accurately determined.

Figure 18:
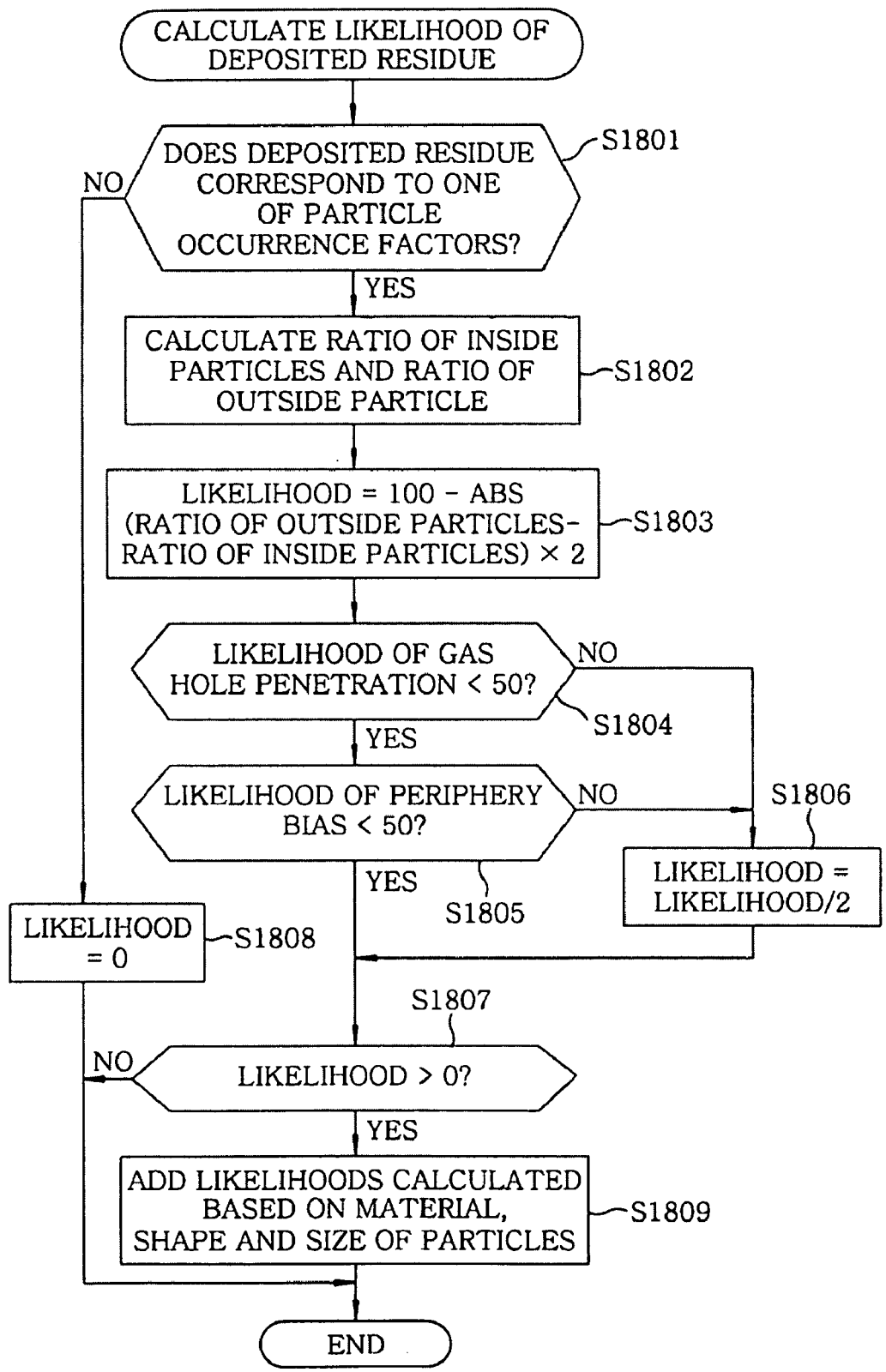
FIG. 18 is a flowchart showing a likelihood calculation process regarding deposited residue.

FIG. 18 is a flowchart showing a likelihood calculation process regarding deposited residue at step S510 of FIG. 5. The deposited residue is minute dregs deposited on the surface of the wafer W. The corresponding dregs grow when the wafer W is left in the atmosphere, thus becoming particles. Furthermore, minute dregs on the surface of the wafer W are randomly deposited on the entire surface of the wafer W. Accordingly, in the processing of FIG. 18, a likelihood is calculated based on the net distribution of particles on the surface of the wafer W, paricularly based on the ratio of inside particles and the ratio of outside particles.

Here, the deposited residue may not be generated depending on the type of the substrate processing system 10. For this reason, in FIG. 18, it is first determined whether the deposited residue is one of the occurrence factors of particles based on the name of the substrate processing system 10, which has been acquired from the client PC 47, at step S1801.

If, as a result of the determination at step S1801, the deposited residue is determined to be one of the occurrence factors of particles, the ratio of inside particles and the ratio of outside particles are calculated at step S1802. Here, the ratio of the inside particles and the ratio of the outside particles are respectively equal to the ratio of the inside particles and the ratio of the outside particles in the respective processings of FIGS. 14 and 16.

A likelihood is calculated using the following equation at step S1803:

$$\text{Likelihood} = 100 - \text{ABS (the ratio of outside particles} - \text{the ratio of inside particles)} \times 2$$

In this case, the ABS denotes an absolute value.

It is then determined whether a likelihood of the gas hole penetration is less than 50 at step S1804. If, as a result of the determination at step S1804, the likelihood of the gas hole penetration is determined to be less than 50, it is determined whether a likelihood of periphery bias is less than 50 at step S1805. If, as a result of the determination at step S1805, the likelihood of the periphery bias is determined to be less than 50, the process proceeds to step S1807 without change.

If, as a result of the determination at step S1804, the likelihood of the gas hole penetration is determined to be 50 or more, and if, as a result of the determination at step S1805, the likelihood of the periphery bias is determined to be 50 or more, the calculated likelihood is divided by 2 and the process proceeds to step S1807.

It is then determined whether the calculated likelihood is more than 0 at step S1807. If, as a result of the determination at step S1807, the calculated likelihood is determined to be 0, the process is terminated. If, as a result of the determination at step S1807, the calculated likelihood is determined to be more than 0, the likelihood of a corresponding one of the occurrence factors of particles, which has been calculated based on the material, shape and size of the particles, is added to the calculated likelihood, as in step S706, at step S1809, and the process is terminated.

Meanwhile, if, as a result of the determination at step S1801, the deposited residue is determined not to be one of the occurrence factors of particles, a likelihood of the deposited residue is set to 0 at step S1808, and the process is terminated.

In accordance with the processing of FIG. 18, a likelihood is calculated based on the ratio of inside particles and the ratio of outside particles. Accordingly, a likelihood about whether particles have been generated by deposited residue can be accurately calculated. As a result, a possibility that the deposited residue may be one of the occurrence factors of particles can be accurately determined.

Figure 19:
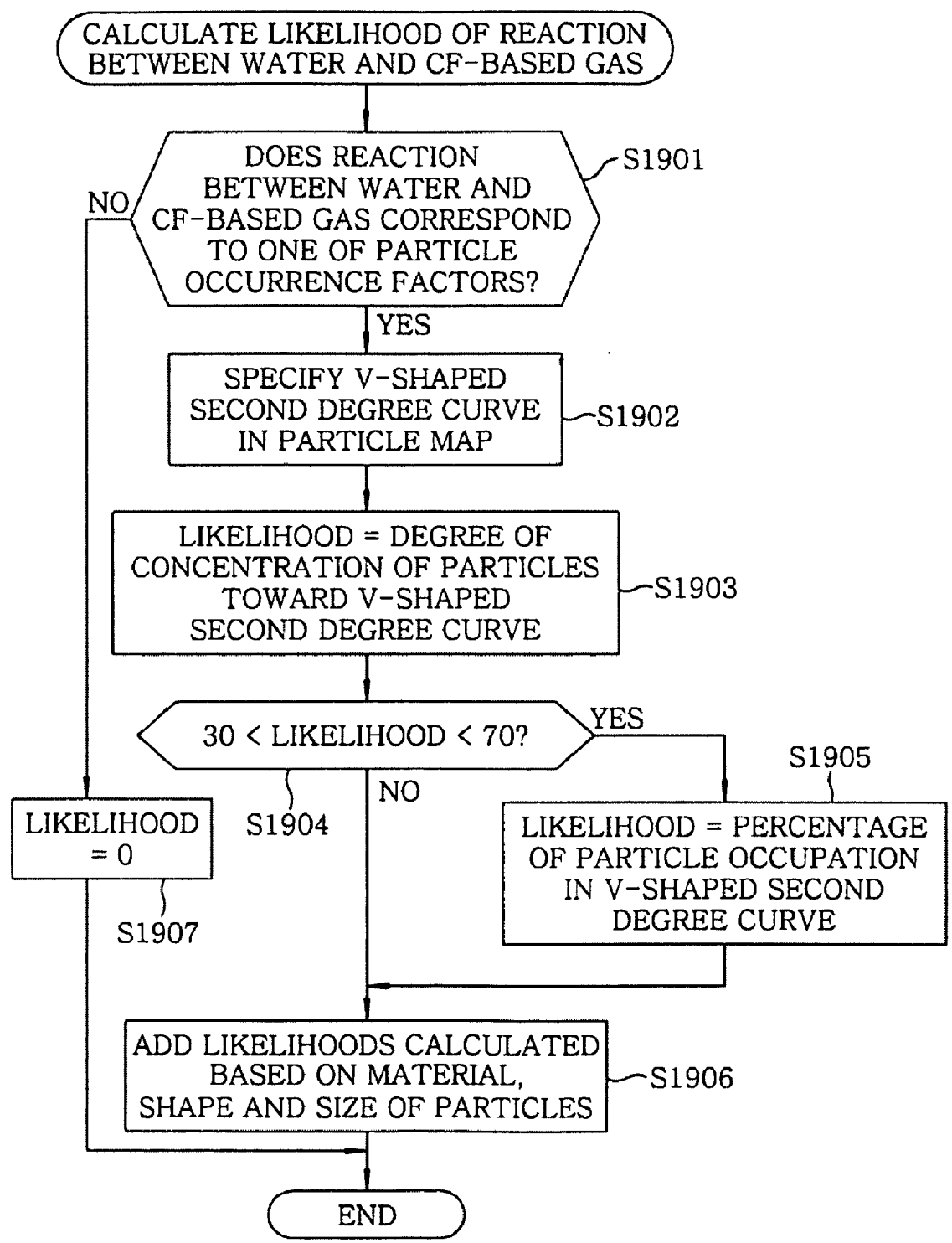
FIG. 19 is a flowchart showing a likelihood calculation process regarding the reaction between water and CF-based gas.

FIG. 19 is a flowchart showing a likelihood calculation process regarding the reaction between water and CF-based gas at step S511 of FIG. 5. If a CF-based gas present among the processing gases remains within the chamber 27 and reacts with water, reactants are created. The corresponding reactants adhere to the surface of the wafer W in the form of particles. In this case, the adhered particles are distributed on the surface of the wafer W in the form of a second degree curve. Accordingly, in the processing of FIG. 19, a likelihood is calculated based on the distribution of a second degree curve of the particles on the surface of the wafer W.

In this case, the reaction between water and CF-based gas may not be generated depending on the type of the substrate processing system 10. For this reason, in FIG. 19, it is first determined whether the reaction between water and CF-based gas is one of the occurrence factors of particles based on the name of the substrate processing system 10, which has been acquired from the client PC 47, at step S1901.

If, as a result of the determination at step S1901, the reaction between water and CF-based gas is determined to be one of the occurrence factors of particles, a V-shaped second degree curve is specified in the particle map at step S1902.

Figure 20A:
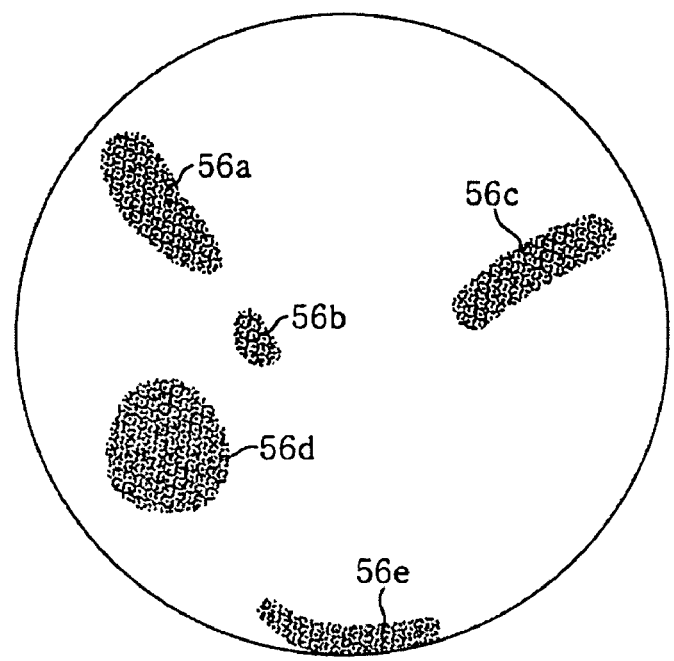
Figure 20B:
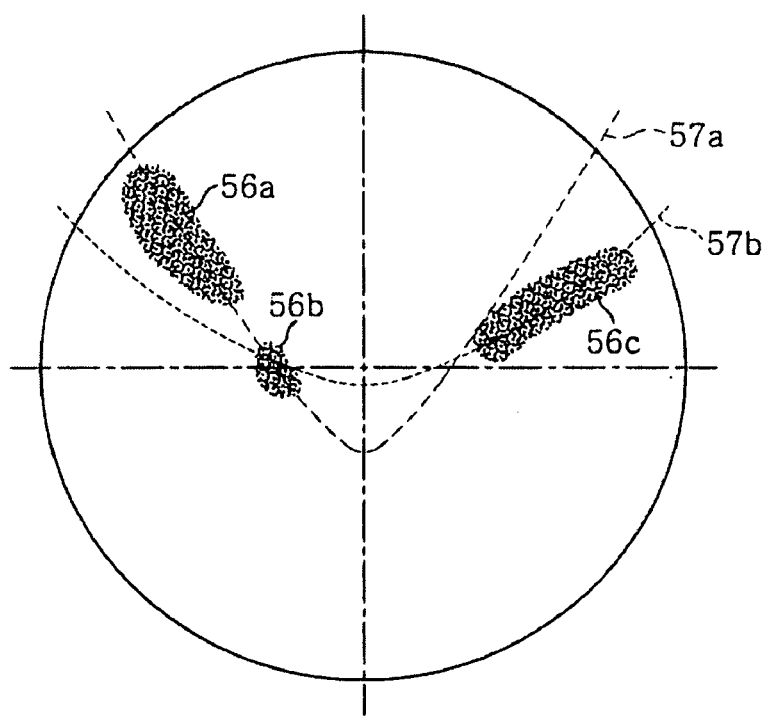

FIGS. 20A and 20B are diagrams illustrating the designation of a V-shaped second degree curve at step S1902.

In FIG. 20A, there are particle groups 56a to 56e indicated by a dark color on the particle map. A second degree curve is first approximately calculated based on the particle groups 56a to 56e. In this case, the second degree curve has a V shape and passes through particle groups existing in the outer peripheral portions (particle groups existing in an area having a radius of 275 mm or more in the particle map), particle groups each having an area of a specific value or less in the particle map, and each particle group in the coordinate system in which the center of the particle map is the origin of the system. Next, particle groups which do not include all particles in a belt having a width of 40 mm in which the corresponding V-shaped second degree curve is a central line are excluded.

Furthermore, second degree curves 57a and 57b, which have a V shape and pass through the particle groups 56a, 56b and 56c not excluded as shown in FIG. 20B, are approximately calculated and then plotted on the particle map. Here, the second degree curve 57a, which has the V shape and passes through each of the particle groups, is calculated between particle groups (for example, the particle groups 56a and 56b) to which the calculated V-shaped second degree curve makes an approach.

A likelihood is then calculated using the following equation at step S1903, and the process proceeds to step S1904.

$$\text{Likelihood} = \text{the degree of concentration of particles onto a V-shaped second degree curve}$$

Here, the degree of concentration of particles onto the V-shaped second degree curve is calculated using the following equation:

The degree of concentration of particles onto the V-shaped second degree curve=the number of particles 15 mm or less away from the V-shaped second degree curve in a particle group/the number of particles 30 mm away from the V-shaped second degree curve in the particle group×100

It is then determined whether the calculated likelihood is more than 30 and less than 70 at step S1904. If, as a result of the determination at step S1904, the calculated likelihood is determined to be 30 or less and 70 or more, the process proceeds to step S1906 without change. If, as a result of the determination at step S1904, the calculated likelihood is determined to be more than 30 and less than 70, a likelihood of the reaction between water and CF-based gas is calculated using the following equation at step S1905. The process then proceeds to step S1906.

Likelihood=the percentage of occupation of particles in a V-shaped second degree curve Here, the percentage of occupation of particles in the V-shaped second degree curve is a ratio of the entire length of the V-shaped second degree curve to the length of a portion in which particles exist in the particle group in the V-shaped second degree curve.

Next, the likelihood of a corresponding one of the occurrence factors of particles, which has been calculated based on the material, shape and size of the particles, is added to the calculated likelihood, as in step S706, at step S1906, and the process is terminated.

Meanwhile, if, as a result of the determination at step S1901, the reaction between water and CF-based gas is determined not to be one of the occurrence factors of particles, a likelihood of the reaction between water and CF-based gas is set to 0 at step S1907, and the process is terminated.

In accordance with the processing of FIG. 19, a likelihood is calculated based on the distribution of particles having a second degree curve on the surface of the wafer W. Accordingly, a likelihood about whether particles have been generated by the reaction between water and CF-based gas can be accurately calculated. As a result, a possibility that the reaction between water and CF-based gas may be one of the occurrence factors of particles can be accurately determined.

Figure 21:
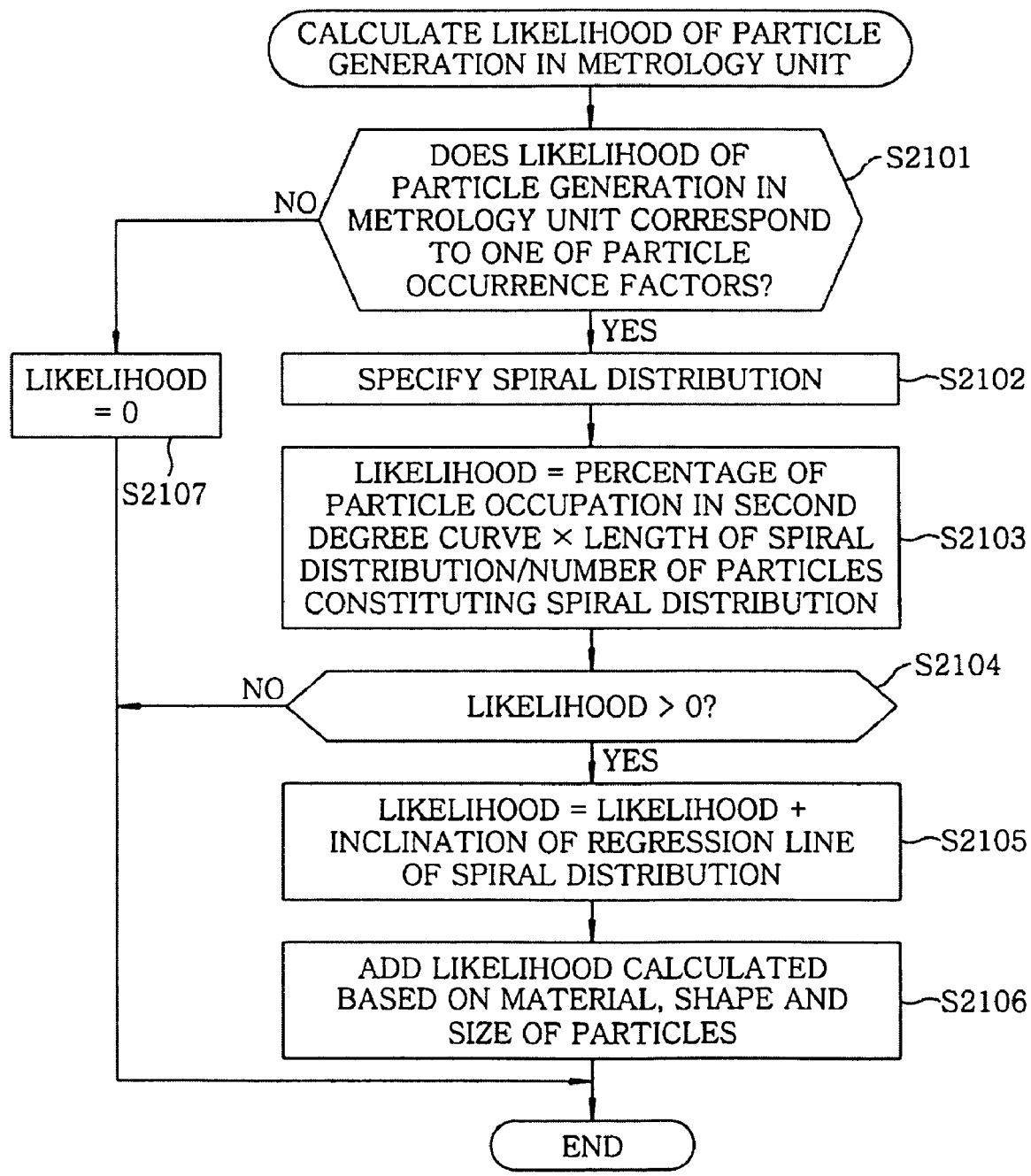
FIG. 21 is a flowchart showing a likelihood calculation process regarding particles generated in a metrology unit.

FIG. 21 is a flowchart showing a likelihood calculation processing regarding particles generated in the metrology unit at step S512 of FIG. 5. If the wafer W is electrically charged, particles which are generated and are floating within the metrology unit 24 may be attracted by the surface of the wafer W and adhere thereto. Furthermore, in the metrology unit 24, when the surface of the wafer W is tested, the wafer W is mounted on the rotary stand 25 and rotated. Accordingly, the particles adhering to the surface of the wafer W are distributed in a spiral arrangement. Accordingly, in the processing of FIG. 21, a likelihood is calculated based on the spiral distributions of the particles on the surface of the wafer W.

Here, the metrology unit 24 may not be included depending on the type of the substrate processing system 10. For this reason, FIG. 21, it is first determined whether the particles generated in the metrology unit are one of the occurrence factors of particles based on the name of the substrate processing system 10, which has been acquired from the client PC 47, at step S2101.

If, as a result of the determination at step S2101, the particles generated in the metrology unit are determined to be one of the occurrence factors of particles, the spiral distributions are specified on the particle map at step S2102.

Figure 22A:
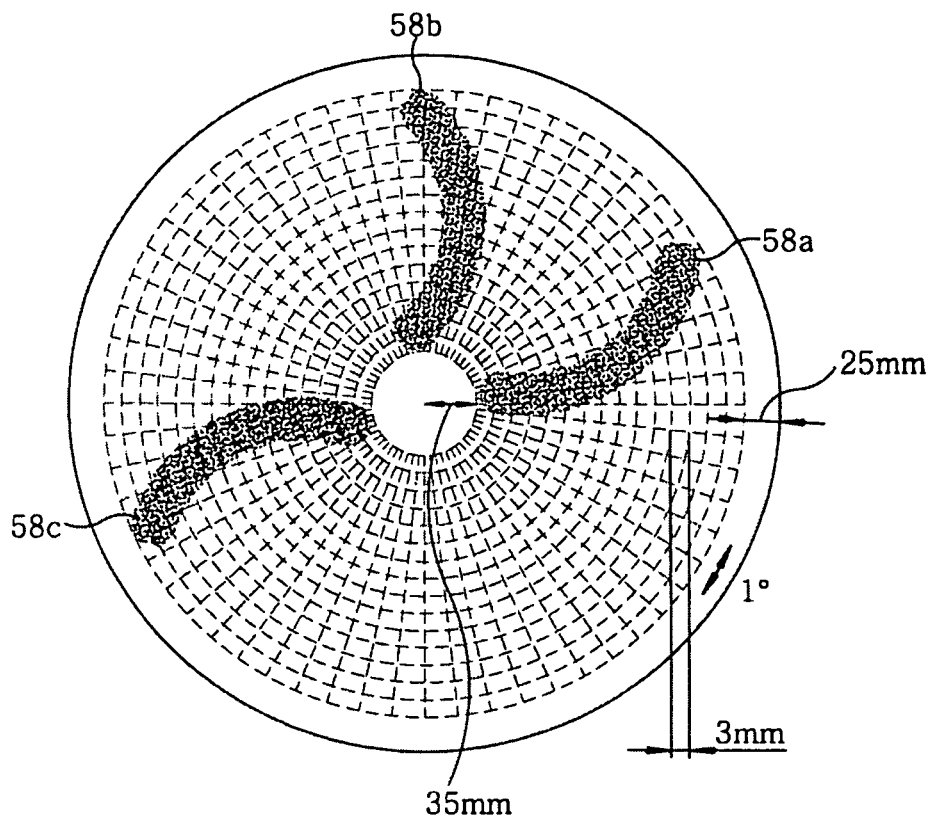
Figure 22B:
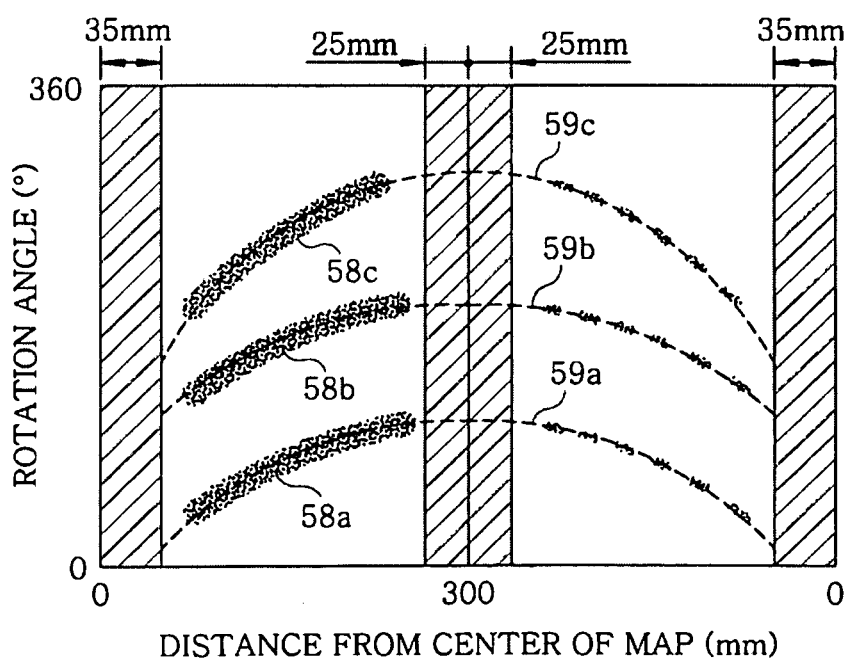

FIGS. 22A and 22B are diagrams illustrating the specification of the spiral distributions at step S2102.

In FIG. 22A, the spiral distributions 58a to 58c of the particles indicated by a dark color exist on the particle map. Particles existing in the outer peripheral portions of the particle map (particles existing in an area outside a radius of 275 mm or more in the particle map) and particles existing at the central portion of the particle map (particles existing in an area having a radius of 35 mm or less in the particle map) are excluded from the spiral distributions 58a to 58c.

Furthermore, the particle map is decomposed into meshes using a lattice. Each of the meshes has a radial length of 3 mm and has a rotation angle of 1° in the case where the center of the particle map is a rotation center (FIG. 22A). Each of the meshes is converted into a coordinate system in which the x axis denotes the distance from the center of the particle map and the y axis denotes the rotation angle in the case where the center of particles is the rotation center (hereinafter referred to as a "conversion coordinate system") (FIG. 22B; however, the edge line of each mesh is omitted). The conversion coordinate system is then symmetrically copied in relation to the line where x=300 mm. In a coordinate system in which the conversion coordinate system and the copied conversion coordinate system are arranged (hereinafter referred to as an "enlarged coordinate system"), second degree curves 59a to 59c passing through the respective spiral distributions 58a to 58c are approximately calculated. In each of the second degree curves, spiral distributions in each of which a length occupied by meshes including particles (meshes corresponding to the spiral distributions) is 50% or less of a total length of the second degree curve or spiral distributions in each of which a length in the x axis direction is 20 mm or less are removed from the enlarged coordinate system. Furthermore, spiral distributions adjacent to each other are combined with each other under certain conditions.

A likelihood is then calculated using the following equation at step S2103, and the process proceeds to step S2104.

Likelihood=the percentage of occupation of particles in a second degree curve×the length of a spiral distribution/the number of particles constituting the spiral distribution Here, the percentage of occupation of particles in the second degree curve is a ratio of a total length of the second degree curve in the enlarged coordinate system to a length occupied by meshes, including particles (meshes corresponding to spiral distributions), in the second degree curve.

It is then determined whether the calculated likelihood is more than 0 at step S2104. If, as a result of the determination at step S2104, the calculated likelihood is determined to be 0, the process is terminated. If, as a result of the determination at step S2104, the calculated likelihood is determined to be more than 0, a regression line is found from the spiral distributions in the enlarged coordinate system, and the inclination of the corresponding regression line is added to the calculated likelihood at step S2105.

Next, the likelihood of a corresponding one of the occurrence factors of particles, which has been calculated based on the material, shape and size of the particles, is added to the calculated likelihood, as in step S706, at step S2106, and the process is terminated.

Meanwhile, if, as a result of the determination at step S2101, the generation of particles in the metrology unit is determined not to be one of the occurrence factors of particles, a likelihood of the particles generated in the metrology unit is set to 0 at step S2107, and the process is terminated.

In accordance with the processing of FIG. 21, a likelihood is calculated based on the spiral distributions of particles on the surface of the wafer W. Accordingly, a likelihood about whether particles have been generated in the metrology unit can be accurately calculated. As a result, a possibility that particles generated in the metrology unit may be one of the occurrence factors of particles can be accurately determined.

Furthermore, in the above-described likelihood calculation process regarding sliding against the focus ring of FIG. 9, the above-described likelihood calculation process regarding an attacked shoulder of the focus ring of FIG. 11, the above-described likelihood calculation process regarding the gas hole penetration of FIG. 12, the above-described likelihood calculation process regarding periphery bias of FIGS. 14A and 14B, the above-described likelihood calculation process regarding COPs of FIG. 16, the above-described likelihood calculation process regarding deposited residue of FIG. 18, the above-described likelihood calculation process regarding the reaction between water and CF-based gas of FIG. 19, and the above-described likelihood calculation process regarding particles generated in the metrology unit of FIG. 21, the likelihoods regarding the respective occurrence factors of particles are calculated based on a name of the substrate processing system 10 (steps S901, S1101, S1201, S1401, S1601, S1801, S1901, and S2101). Accordingly, likelihoods for occurrence factors of particles, which cannot occur, are not calculated in the target substrate processing system 10. As a result, the occurrence factors of particles can be accurately determined.

Furthermore, although in the above-described embodiments, the substrate on which an etching process is performed has been described as the semiconductor wafer W, the substrate on which the etching processing is performed is not limited to the semiconductor wafer W, but may include, for example, a glass substrate, such as a Liquid Crystal Display (LCD) or a Flat Panel Display (FPD).

Furthermore, another object of the present invention is achieved in such a way that recording media in which software programs for realizing the above-described functions of the present embodiments are recorded are provided to a computer and then the CPU of the computer reads and executes the programs recorded on the recording media.

In this case, the programs themselves read from the recording media implement the above-described functions of the present embodiments. The programs and the recording media in which the programs are recorded constitute the present invention.

Furthermore, the recording media for supplying the programs may include, for example, RAM, NV-RAM, floppy (registered trademark) disks, hard disks, magneto-optical disks, optical disks such as CD-ROM, CDs-R, CDs-RW, or DVDs (DVDs-ROM, DVDs-RAM, DVDs-RW and DVDs+RW), magnetic tapes, nonvolatile memory cards, and other ROM, which are capable of storing the above programs. Alternatively, the programs may be supplied to a computer by downloading the programs from another computer or from a database (not shown) connected to the Internet, a commercial network, or a Local Area Network (LAN).

Furthermore, the present invention includes not only the case where the functions of the present embodiments are realized by a computer for executing the read programs, but also the case where the above-described functions of the present embodiments are realized in such a way that an Operating System (OS) operating on a CPU executes part or all of the actual processing according to the command of the program.

Furthermore, the present invention includes the case where the above-described functions of the present embodiments are realized in such a manner that the programs read from the recording media are written in memory, which is included in a function extension board inserted into a computer or in a function extension unit connected to the computer and a CPU included in the function extension board or in the function extension board executes part or all of the actual processing according to the command of the program.

The programs may be in the form of object code, programs executable by an interpreter, or script data supplied to an OS.

While the invention has been shown and described with respect to the preferred embodiment, it will be understood by those skilled in the art that various changes and modifications may be made without departing from the scope of the invention as defined in the following claims.

What is claimed is:

1. A system for determining one or more occurrence factors of particles, comprising:
    a user interface device; and
    an apparatus for detecting the occurrence factors of particles,
    wherein the apparatus for detecting the occurrence factors of particles includes:
    a storage unit that stores a program for executing a calculation method for calculating a probability of each of the occurrence factors of particles in the form of a quantified score; and
    a calculation unit for determining whether to calculate the quantified score depending on a type of a substrate processing system using the stored program and calculating the quantified score for each of the occurrence factors of particles based on particle distributions at least on a surface of a substrate using the stored program,
    wherein the user interface device displays the calculated quantified score for each of the occurrence factors of particles,
    wherein the calculation unit determines a dominant occurrence factor of particles based on quantified scores calculated by using the following calculation methods (i) to (iv);
    the calculation method (i) wherein the quantified score is calculated based on deviation between placement positions of gas holes of a shower head for supplying a processing gas in each of process modules of the substrate processing system and positions of a particle distributions on the surface of the substrate,
    the calculation method (ii) wherein the quantified score is calculated based on the number of particles distributed on a surface at a central portion of the substrate and the number of particles distributed on a surface in the peripheral portions of the substrate,
    the calculation method (iii) wherein the quantified score is calculated based on distributions of second degree curves of the particles on the surface of the substrate, and
    the calculation method (iv) wherein the quantified score is calculated based on spiral distributions of the particles on the surface of the substrate wherein the occurrence factors of particles respectively corresponding to the programs for executing the calculation methods stored in the storage unit include at least one of gas hole penetration, deposited residue, and a reaction between water and halogen-based gas, and particles generated in a measurement unit having a rotary device for rotating the substrate, wherein the calculation methods (i) to (iv) are respectively employed in calculating a probability of the gas hole penetration, a probability of the deposited residue, a probability of the reaction between water and halogen-based gas and a probability of the particles generated in a measurement unit having a rotary device for rotating the substrate.

2. The system of claim 1, wherein the calculation unit calculates the quantified score based on at least one of a material, shape and size of the particles.

3. The system of claim 1, wherein the storage unit is capable of storing a program for executing a calculation method for calculating a probability of a new occurrence factor of particles in the form of a quantified score.

4. The system of claim 1, wherein the user interface device displays the particle distributions on the surface of the substrate and displays a color, shape, size, brightness or display type of the particles pertinent to the respective occurrence factor of particles in the particle distributions differently from a color, shape, size, brightness or display type of the particles pertinent to other remaining occurrence factors of particles, and wherein the display type is either blink or non-blink.

5. The system of claim 1, wherein the user interface device displays a countermeasure method for each of the occurrence factors of particles.

6. A system for determining one or more occurrence factors of particles, comprising:
a user interface device; and
an apparatus for detecting the occurrence factors of particles, wherein the apparatus for detecting the occurrence factors of particles includes:
a storage unit that stores a program for executing a calculation method for calculating a probability of each of the occurrence factors of particles in the form of a score; and
a calculation unit for determining whether to calculate the score depending on a type of a substrate processing system using the stored program and calculating the score for each of the occurrence factors of particles based on particle distributions at least on a surface of a substrate using the stored program,
wherein the user interface device displays the calculated score for each of the occurrence factors of particles,
wherein the calculation unit determines the occurrence factors of particles by using at least one of the following calculation methods (i) and (ii):
the calculation method (i) wherein the score is calculated based on deviation between placement positions of gas holes of a shower head for supplying a processing gas in each of process modules of the substrate processing system and positions of a particle distributions on the surface of the substrate, and
the calculation method (ii) wherein the score is calculated based on distributions of second degree curves of the particles on the surface of the substrate
wherein the occurrence factors of particles respectively corresponding to the programs for executing the calculation methods stored in the storage unit include at least one of gas hole penetration and a reaction between water and halogen-based gas, and
wherein the calculation methods (i) and (ii) are respectively employed in calculating a probability of the gas hole penetration and a probability of the reaction between water and halogen-based gas.

7. A method of determining occurrence factors of particles, the method comprising:
reading a program for executing a calculation method by using CPU of a host server for calculating a probability of each of the occurrence factors of particles in the form of a quantified score;
calculating the quantified score for each of the occurrence factors of particles by using CPU of a host server based on particle distributions at least on a surface of a substrate using the read program; and displaying the quantified score calculated for each of the occurrence factors of particles by using a user interface device,
wherein the occurrence factors of particles respectively corresponding to the programs for executing the calculation methods stored in the storage unit include gas hole penetration, deposited residue, a reaction between water and halogen-based gas, and particles generated in a measurement unit having a rotary device for rotating the substrate,
wherein, in a calculation method for calculating a probability of the gas hole penetration in the form of a first quantified score, the first quantified score is calculated based on deviation between placement positions of the gas holes of a shower head for supplying a processing gas in each of process modules of the substrate processing system and positions of the particle distributions on the surface of the substrate,
wherein, in a calculation method for calculating a probability of the deposited residue in the form of a second quantified score, the second quantified score is calculated based on the number of particles distributed on a surface at a central portion of the substrate and the number of particles distributed on a surface in the peripheral portions of the substrate,
wherein, in a calculation method for calculating a probability of the reaction between water and halogen-based gas in the form of a third quantified score, the third quantified score is calculated based on distributions of second degree curves of the particles on the surface of the substrate, and
wherein, in a calculation method for calculating a probability of the particles generated in the measurement unit having the rotary device for rotating the substrate in the form of a fourth quantified score, the fourth quantified score is calculated based on spiral distributions of the particles on the surface of the substrate.

8. A non-transitory computer-readable storage medium including computer executable instructions, wherein the instructions, when executed by a computer, cause the processor to perform a method of determining occurrence factors of particles, the method comprising:
reading a program for executing a calculation method by using CPU of a host server for calculating a probability of each of the occurrence factors of particles in the form of a quantified score;
calculating the quantified score for each of the occurrence factors of particles by using CPU of a host server based on particle distributions at least on a surface of a substrate using the read program; and
displaying the quantified score calculated for each of the occurrence factors of particles by using a user interface device,
wherein the occurrence factors of particles respectively corresponding to the programs for executing the calculation methods stored in the storage unit include gas hole penetration, deposited residue, a reaction between water and halogen-based gas, and particles generated in a measurement unit having a rotary device for rotating the substrate,
wherein, in a calculation method for calculating a probability of the gas hole penetration in the form of a first quantified score, the first quantified score is calculated based on deviation between placement positions of the gas holes of a shower head for supplying a processing gas in each of process modules of the substrate processing system and positions of the particle distributions on the surface of the substrate, wherein, in a calculation method for calculating a probability of the deposited residue in the form of a second quantified score, the second quantified score is calculated based on the number of particles distributed on a surface at a central portion of the substrate and the number of particles distributed on a surface in the peripheral portions of the substrate, wherein, in a calculation method for calculating a probability of the reaction between water and halogen-based gas in the form of a third quantified score, the third quantified score is calculated based on distributions of second degree curves of the particles on the surface of the substrate, and wherein, in a calculation method for calculating a probability of the particles generated in the measurement unit having the rotary device for rotating the substrate in the form of a fourth quantified score, the fourth quantified score is calculated based on spiral distributions of the particles on the surface of the substrate.

* * * * *